(12) United States Patent
Wu et al.

(10) Patent No.: US 9,770,204 B2
(45) Date of Patent: Sep. 26, 2017

(54) DEEP BRAIN STIMULATION FOR SLEEP AND MOVEMENT DISORDERS

(75) Inventors: Jianping Wu, Shoreview, MN (US); Dwight E. Nelson, Shoreview, MN (US); Xin Su, Shoreview, MN (US); Gregory F. Molnar, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 2097 days.

(21) Appl. No.: 12/616,513

(22) Filed: Nov. 11, 2009

(65) Prior Publication Data

US 2011/0112590 A1    May 12, 2011

(51) Int. Cl.
*A61N 1/36* (2006.01)
*A61B 5/00* (2006.01)
*A61N 1/05* (2006.01)

(52) U.S. Cl.
CPC ........ *A61B 5/4812* (2013.01); *A61N 1/36082* (2013.01); *A61B 5/4082* (2013.01); *A61N 1/0534* (2013.01); *A61N 1/36078* (2013.01)

(58) Field of Classification Search
CPC ........................ A61N 1/36078; A61N 1/36082
USPC ...................................................... 607/2, 45
See application file for complete search history.

(56) References Cited

U.S. PATENT DOCUMENTS

| | | |
|---|---|---|
| 1,342,885 A | 6/1920 | Armstrong |
| 3,130,373 A | 4/1964 | Braymer |
| 3,603,997 A | 9/1971 | Brouwer et al. |
| 3,780,725 A | 12/1973 | Goldberg |
| 4,013,068 A | 3/1977 | Settle et al. |
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |

(Continued)

FOREIGN PATENT DOCUMENTS

| | | |
|---|---|---|
| CN | 86102707 A | 11/1986 |
| CN | 86102810 A | 11/1986 |

(Continued)

OTHER PUBLICATIONS

Notification of Transmittal of the International Search Report and the Written Opinion of the International Searching Authority for corresponding patent application No. PCT/2010/055943, mailed Feb. 1, 2011, 11 pages.

(Continued)

*Primary Examiner* — Eric D. Bertram
(74) *Attorney, Agent, or Firm* — Shumaker & Sieffert, P.A.

(57) ABSTRACT

Delivery of electrical stimulation to the substantia nigra and the subthalamic nucleus of a brain of a patient are independently controlled in order to treat sleep and movement disorders. Electrical stimulation of the subthalamic nucleus may be effective in treating symptoms associated with a movement disorder, and electrical stimulation of the substantia nigra may be effective in treating symptoms associated with a sleep disorder. During a sleep state of the patient, a sleep stage of the patient may be determined, and an electrical stimulation device may be controlled based on the determined sleep stage. Electrical stimulation of the substantia nigra and subthalamic nucleus may be delivered at substantially the same time or at different times.

28 Claims, 9 Drawing Sheets

(56) References Cited

U.S. PATENT DOCUMENTS

| | | |
|---|---|---|
| 4,610,259 A | 9/1986 | Cohen et al. |
| 4,612,934 A | 9/1986 | Borkan |
| 4,733,667 A | 3/1988 | Olive et al. |
| 4,776,345 A | 10/1988 | Cohen et al. |
| 4,933,642 A | 6/1990 | Lee |
| 4,979,230 A | 12/1990 | Marz |
| 5,024,221 A | 6/1991 | Morgan |
| 5,061,593 A | 10/1991 | Yoerger et al. |
| 5,105,167 A | 4/1992 | Peczalski |
| 5,113,143 A | 5/1992 | Wei |
| 5,154,180 A | 10/1992 | Blanchet et al. |
| 5,179,947 A | 1/1993 | Meyerson et al. |
| 5,205,285 A | 4/1993 | Baker, Jr. |
| 5,206,602 A | 4/1993 | Baumgartner et al. |
| 5,215,086 A | 6/1993 | Terry, Jr. et al. |
| 5,282,840 A | 2/1994 | Hudrlik |
| 5,293,879 A | 3/1994 | Vonk et al. |
| 5,299,569 A | 4/1994 | Wernicke |
| 5,311,876 A | 5/1994 | Olsen et al. |
| 5,334,222 A | 8/1994 | Salo et al. |
| 5,335,657 A | 8/1994 | Terry, Jr. et al. |
| 5,458,117 A | 10/1995 | Chamoun et al. |
| 5,477,481 A | 12/1995 | Kerth |
| 5,489,759 A | 2/1996 | Litt et al. |
| 5,619,536 A | 4/1997 | Gourgue |
| 5,663,680 A | 9/1997 | Nordeng |
| 5,716,377 A | 2/1998 | Rise et al. |
| 5,725,558 A | 3/1998 | Warnke |
| 5,769,877 A | 6/1998 | Barreras, Sr. |
| 5,782,884 A | 7/1998 | Stotts et al. |
| 5,833,709 A | 11/1998 | Rise et al. |
| 5,840,040 A | 11/1998 | Altschuler et al. |
| 5,843,139 A | 12/1998 | Goedeke et al. |
| 5,928,272 A | 7/1999 | Adkins et al. |
| 5,995,868 A | 11/1999 | Dorfmeister et al. |
| 6,011,990 A | 1/2000 | Schultz et al. |
| 6,018,682 A | 1/2000 | Rise |
| 6,024,700 A | 2/2000 | Nemirovski et al. |
| 6,061,593 A | 5/2000 | Fischell et al. |
| 6,064,257 A | 5/2000 | Sauer |
| 6,066,163 A | 5/2000 | John |
| 6,070,101 A | 5/2000 | Struble et al. |
| 6,094,598 A | 7/2000 | Elsberry et al. |
| 6,129,681 A | 10/2000 | Kuroda et al. |
| 6,130,578 A | 10/2000 | Tang |
| 6,157,857 A | 12/2000 | Dimpfel |
| 6,161,042 A | 12/2000 | Hartley et al. |
| 6,214,016 B1 | 4/2001 | Williams et al. |
| 6,262,626 B1 | 7/2001 | Bakker et al. |
| 6,272,378 B1 | 8/2001 | Baumgart-Schmitt |
| 6,287,263 B1 | 9/2001 | Briskin |
| 6,315,740 B1 | 11/2001 | Slingh |
| 6,331,160 B1 | 12/2001 | Bardy |
| 6,353,762 B1 | 3/2002 | Baudino et al. |
| 6,356,784 B1 | 3/2002 | Lozano et al. |
| 6,360,123 B1 | 3/2002 | Kimchi et al. |
| 6,366,813 B1 | 4/2002 | DiLorenzo |
| 6,456,159 B1 | 9/2002 | Brewer |
| 6,459,936 B2 | 10/2002 | Fischell et al. |
| 6,463,328 B1 | 10/2002 | John |
| 6,468,234 B1 | 10/2002 | Van der Loos et al. |
| 6,483,355 B1 | 11/2002 | Lee et al. |
| 6,522,914 B1 | 2/2003 | Huvelle et al. |
| 6,539,261 B2 | 3/2003 | Dal Molin |
| 6,584,351 B1 | 6/2003 | Ekwall |
| 6,597,953 B2 | 7/2003 | Boling |
| 6,605,038 B1 | 8/2003 | Teller et al. |
| 6,617,838 B1 | 9/2003 | Miranda et al. |
| 6,625,436 B1 | 9/2003 | Tolson et al. |
| 6,658,287 B1 | 12/2003 | Litt et al. |
| 6,667,760 B1 | 12/2003 | Limberg |
| 6,674,322 B2 | 1/2004 | Motz |
| 6,725,091 B2 | 4/2004 | Dal Molin |
| 6,754,535 B2 | 6/2004 | Noren et al. |
| 6,810,285 B2 | 10/2004 | Pless et al. |
| 6,819,956 B2 | 11/2004 | DiLorenzo |
| 6,839,594 B2 | 1/2005 | Cohen et al. |
| 6,876,842 B2 | 4/2005 | Davie |
| 6,904,321 B1 | 6/2005 | Bornzin et al. |
| 6,914,539 B2 | 7/2005 | Hoctor et al. |
| 6,954,524 B2 | 10/2005 | Gibson |
| 6,993,380 B1 | 1/2006 | Modarres |
| 7,006,872 B2 | 2/2006 | Gielen et al. |
| 7,010,347 B2 | 3/2006 | Schecter |
| 7,098,823 B2 | 8/2006 | O'Dowd et al. |
| 7,110,820 B2 | 9/2006 | Tcheng et al. |
| 7,120,486 B2 | 10/2006 | Leuthardt et al. |
| 7,142,917 B2 | 11/2006 | Fukui |
| 7,146,208 B2 | 12/2006 | Holmstrom et al. |
| 7,146,218 B2 | 12/2006 | Esteller et al. |
| 7,151,961 B1 | 12/2006 | Whitehurst et al. |
| 7,171,258 B2 | 1/2007 | Goode |
| 7,177,609 B1 | 2/2007 | Wong |
| 7,209,788 B2 | 4/2007 | Nicolelis et al. |
| 7,233,198 B2 | 6/2007 | Niederkorn |
| 7,239,927 B2 | 7/2007 | Ganion |
| 7,299,088 B1 | 11/2007 | Thakor et al. |
| 7,376,463 B2 | 5/2008 | Salo et al. |
| 7,385,443 B1 | 6/2008 | Denison |
| 7,391,257 B1 | 6/2008 | Denison et al. |
| 7,491,181 B2 | 2/2009 | Heruth et al. |
| 7,519,431 B2 | 4/2009 | Goetz et al. |
| 7,595,648 B2 | 9/2009 | Ungaretti et al. |
| 7,622,988 B2 | 11/2009 | Denison et al. |
| 7,671,672 B2 | 3/2010 | McConnell |
| 7,684,867 B2 | 3/2010 | Jaax et al. |
| 7,769,464 B2 | 8/2010 | Gerber et al. |
| 7,813,802 B2 | 10/2010 | Tcheng et al. |
| 7,826,894 B2 | 11/2010 | Musallam et al. |
| 7,847,628 B2 | 12/2010 | Denison |
| 7,957,814 B2 | 6/2011 | Goetz et al. |
| 7,974,703 B2 | 7/2011 | Goetz et al. |
| 8,032,229 B2 | 10/2011 | Gerber et al. |
| 8,121,694 B2 | 2/2012 | Molnar et al. |
| 8,290,596 B2 | 10/2012 | Wei et al. |
| 8,380,314 B2 | 2/2013 | Panken et al. |
| 8,554,325 B2 | 10/2013 | Molnar et al. |
| 8,738,145 B2 | 5/2014 | Goetz et al. |
| 8,751,007 B2 | 6/2014 | Goetz et al. |
| 9,072,870 B2 | 7/2015 | Wu et al. |
| 2002/0002390 A1 | 1/2002 | Fischell et al. |
| 2002/0017782 A1 | 2/2002 | Patton et al. |
| 2002/0038137 A1 | 3/2002 | Stein |
| 2002/0091332 A1 | 7/2002 | Bombardini |
| 2002/0103512 A1 | 8/2002 | Echauz et al. |
| 2002/0177882 A1 | 11/2002 | DiLorenzo |
| 2003/0046254 A1 | 3/2003 | Ryu et al. |
| 2003/0105409 A1 | 6/2003 | Donoghue et al. |
| 2003/0146786 A1 | 8/2003 | Gulati et al. |
| 2003/0149457 A1 | 8/2003 | Tcheng et al. |
| 2003/0158587 A1 | 8/2003 | Esteller et al. |
| 2003/0171791 A1 | 9/2003 | KenKnight et al. |
| 2004/0002635 A1 | 1/2004 | Hargrove et al. |
| 2004/0015211 A1 | 1/2004 | Nurmikko et al. |
| 2004/0077967 A1 | 4/2004 | Jordan |
| 2004/0077987 A1 | 4/2004 | Rapacki et al. |
| 2004/0082875 A1 | 4/2004 | Donoghue et al. |
| 2004/0122483 A1 | 6/2004 | Nathan et al. |
| 2004/0138516 A1 | 7/2004 | Osorio et al. |
| 2004/0141558 A1 | 7/2004 | Plisch et al. |
| 2004/0158119 A1 | 8/2004 | Osorio et al. |
| 2004/0167418 A1 | 8/2004 | Nguyen et al. |
| 2004/0176809 A1 | 9/2004 | Cho et al. |
| 2004/0215286 A1 | 10/2004 | Stypulkowski |
| 2004/0249302 A1 | 12/2004 | Donoghue et al. |
| 2004/0249422 A1 | 12/2004 | Gliner et al. |
| 2005/0007091 A1 | 1/2005 | Makeig et al. |
| 2005/0033376 A1 | 2/2005 | Whitehurst |
| 2005/0043652 A1 | 2/2005 | Lovett et al. |
| 2005/0065427 A1 | 3/2005 | Magill et al. |
| 2005/0080461 A1 | 4/2005 | Stahmann et al. |
| 2005/0081847 A1 | 4/2005 | Lee et al. |
| 2005/0107838 A1 | 5/2005 | Lovett et al. |
| 2005/0113744 A1 | 5/2005 | Donoghue et al. |

(56) References Cited

U.S. PATENT DOCUMENTS

| | | |
|---|---|---|
| 2005/0118968 A1 | 6/2005 | Cowley |
| 2005/0143589 A1 | 6/2005 | Donoghue et al. |
| 2005/0182447 A1 | 8/2005 | Schecter |
| 2005/0197588 A1 | 9/2005 | Freeberg |
| 2005/0203366 A1 | 9/2005 | Donoghue et al. |
| 2005/0209511 A1 | 9/2005 | Heruth et al. |
| 2005/0209512 A1 | 9/2005 | Heruth et al. |
| 2005/0209644 A1 | 9/2005 | Heruth et al. |
| 2005/0216064 A1 | 9/2005 | Heruth et al. |
| 2005/0240242 A1 | 10/2005 | DiLorenzo |
| 2005/0246003 A1 | 11/2005 | Black et al. |
| 2005/0282517 A1 | 12/2005 | Cowley |
| 2006/0041221 A1 | 2/2006 | Stypulkowski |
| 2006/0049957 A1 | 3/2006 | Surgenor et al. |
| 2006/0055456 A1 | 3/2006 | Niederkorn |
| 2006/0058627 A1 | 3/2006 | Flaherty et al. |
| 2006/0106275 A1 | 5/2006 | Raniere |
| 2006/0116591 A1 | 6/2006 | Cooper |
| 2006/0133550 A1 | 6/2006 | Bolton et al. |
| 2006/0135877 A1 | 6/2006 | Giftakis et al. |
| 2006/0135879 A1 | 6/2006 | Liley |
| 2006/0139192 A1 | 6/2006 | Morrow et al. |
| 2006/0139193 A1 | 6/2006 | Morrow et al. |
| 2006/0149338 A1 | 7/2006 | Flaherty et al. |
| 2006/0161219 A1 | 7/2006 | Mock et al. |
| 2006/0167530 A1 | 7/2006 | Flaherty et al. |
| 2006/0169282 A1 | 8/2006 | Izumi et al. |
| 2006/0173259 A1 | 8/2006 | Flaherty et al. |
| 2006/0173494 A1 | 8/2006 | Armstrong et al. |
| 2006/0173501 A1 | 8/2006 | Stickney et al. |
| 2006/0184060 A1 | 8/2006 | Belalcazar et al. |
| 2006/0189899 A1 | 8/2006 | Flaherty et al. |
| 2006/0206167 A1 | 9/2006 | Flaherty et al. |
| 2006/0206174 A1 | 9/2006 | Honeycutt et al. |
| 2006/0212089 A1 | 9/2006 | Tass |
| 2006/0212090 A1 | 9/2006 | Lozano et al. |
| 2006/0212093 A1 | 9/2006 | Pless et al. |
| 2006/0229687 A1 | 10/2006 | Goetz et al. |
| 2006/0241357 A1 | 10/2006 | Chirife |
| 2006/0253166 A1 | 11/2006 | Flaherty et al. |
| 2006/0253168 A1 | 11/2006 | Wyler et al. |
| 2006/0258930 A1 | 11/2006 | Wu et al. |
| 2006/0259099 A1 | 11/2006 | Goetz et al. |
| 2006/0265022 A1 | 11/2006 | John et al. |
| 2006/0281427 A1 | 12/2006 | Isaac et al. |
| 2006/0293604 A1 | 12/2006 | Carlson et al. |
| 2006/0293720 A1 | 12/2006 | DiLorenzo |
| 2007/0010755 A1 | 1/2007 | Sarkela et al. |
| 2007/0016095 A1 | 1/2007 | Low et al. |
| 2007/0032737 A1 | 2/2007 | Causevic et al. |
| 2007/0032738 A1 | 2/2007 | Flaherty et al. |
| 2007/0032834 A1 | 2/2007 | Gliner et al. |
| 2007/0038265 A1 | 2/2007 | Tcheng et al. |
| 2007/0046486 A1 | 3/2007 | Donoghue et al. |
| 2007/0073355 A1 | 3/2007 | Dilorenzo |
| 2007/0077907 A1 | 4/2007 | Rector |
| 2007/0123758 A1 | 5/2007 | Miesel et al. |
| 2007/0150025 A1 | 6/2007 | Dilorenzo et al. |
| 2007/0179534 A1 | 8/2007 | Firlik et al. |
| 2007/0213785 A1 | 9/2007 | Osorio et al. |
| 2007/0216477 A1 | 9/2007 | McConnell |
| 2007/0249953 A1 | 10/2007 | Frei et al. |
| 2008/0015659 A1 | 1/2008 | Zhang et al. |
| 2008/0051839 A1 | 2/2008 | Libbus et al. |
| 2008/0071314 A1 | 3/2008 | John |
| 2008/0077191 A1 | 3/2008 | Morrell |
| 2008/0154111 A1 | 6/2008 | Wu et al. |
| 2008/0180278 A1 | 7/2008 | Denison |
| 2008/0195166 A1 | 8/2008 | Sun et al. |
| 2008/0243005 A1 | 10/2008 | Jung et al. |
| 2008/0269630 A1 | 10/2008 | Denison et al. |
| 2008/0269631 A1 | 10/2008 | Denison et al. |
| 2008/0269812 A1 | 10/2008 | Gerber et al. |
| 2008/0269841 A1 | 10/2008 | Grevious et al. |
| 2009/0018617 A1 | 1/2009 | Skelton et al. |
| 2009/0082691 A1 | 3/2009 | Denison et al. |
| 2009/0082829 A1 | 3/2009 | Panken et al. |
| 2009/0082831 A1 | 3/2009 | Paul et al. |
| 2009/0099627 A1 | 4/2009 | Molnar et al. |
| 2009/0105785 A1 | 4/2009 | Wei et al. |
| 2009/0118786 A1 | 5/2009 | Meadows et al. |
| 2009/0118787 A1 | 5/2009 | Moffitt et al. |
| 2009/0131995 A1 | 5/2009 | Sloan et al. |
| 2009/0192556 A1* | 7/2009 | Wu et al. ................ 607/3 |
| 2009/0264789 A1 | 10/2009 | Molnar et al. |
| 2010/0033240 A1 | 2/2010 | Denison et al. |
| 2010/0113964 A1 | 5/2010 | Wahlstrand et al. |
| 2010/0114223 A1 | 5/2010 | Wahlstrand et al. |
| 2010/0324442 A1 | 12/2010 | Blomqvist |
| 2010/0327887 A1 | 12/2010 | Denison et al. |
| 2011/0004268 A1 | 1/2011 | Tcheng et al. |
| 2011/0015469 A1 | 1/2011 | Walter et al. |
| 2011/0068861 A1 | 3/2011 | Denison |
| 2011/0112590 A1 | 5/2011 | Wu et al. |
| 2011/0230940 A1 | 9/2011 | Goetz et al. |
| 2012/0053508 A1 | 3/2012 | Wu et al. |
| 2013/0131755 A1 | 5/2013 | Panken et al. |

FOREIGN PATENT DOCUMENTS

| | | |
|---|---|---|
| CN | 2683027 Y | 3/2005 |
| CN | 2754557 Y | 2/2006 |
| CN | 2882531 Y | 3/2007 |
| CN | 101099670 A | 1/2008 |
| DE | 196 49 991 | 6/1998 |
| EP | 0354060 A2 | 2/1990 |
| EP | 0 438 945 | 7/1991 |
| EP | 0789449 A2 | 8/1997 |
| EP | 1 943 944 | 7/2008 |
| EP | 2008581 A2 | 12/2008 |
| GB | GB 1249395 A | 10/1971 |
| GB | 2 447 640 | 9/2008 |
| JP | H06224659 A | 8/1994 |
| JP | H07120207 A | 5/1995 |
| JP | H10504099 A | 4/1998 |
| JP | 2006279377 A | 10/2006 |
| JP | 2008-154681 | 7/2008 |
| KR | 2001-0096372 | 11/2001 |
| RU | 2 144 310 | 1/2000 |
| WO | WO 97/10747 A1 | 3/1997 |
| WO | WO 00/10455 A1 | 3/2000 |
| WO | WO 02/01711 A1 | 1/2002 |
| WO | WO 02/03087 A1 | 1/2002 |
| WO | WO 02/49500 A2 | 6/2002 |
| WO | WO 02/058536 A2 | 8/2002 |
| WO | WO 03/101532 A2 | 12/2003 |
| WO | WO 2005/001707 A2 | 1/2005 |
| WO | WO 2005/046469 A2 | 5/2005 |
| WO | 2005/089646 A1 | 9/2005 |
| WO | 2005089641 A1 | 9/2005 |
| WO | WO 2005/092183 A1 | 10/2005 |
| WO | WO 2006/015002 A1 | 2/2006 |
| WO | WO 2006/020794 A2 | 2/2006 |
| WO | WO 2006/066098 A1 | 6/2006 |
| WO | WO 2006/073915 A2 | 7/2006 |
| WO | WO 2006/074029 A2 | 7/2006 |
| WO | WO 2006/076164 A2 | 7/2006 |
| WO | 2006/121455 A1 | 11/2006 |
| WO | WO 2006/126186 A2 | 11/2006 |
| WO | 2007/112092 A2 | 10/2007 |
| WO | WO 2008/103078 A1 | 8/2008 |
| WO | WO 2008/105692 A1 | 9/2008 |
| WO | WO 2009/039294 A1 | 3/2009 |
| WO | 2009042170 A1 | 4/2009 |
| WO | WO 2009/042172 A2 | 4/2009 |
| WO | WO 2009/042313 A2 | 4/2009 |
| WO | 2009/059041 A1 | 5/2009 |

OTHER PUBLICATIONS

Jianping et al.,"Study on Feature Extraction of the Sleep-Multigraph", Journal of Biomedical Engineering, Issue 5, vol. 22, p. 906-909, Dec. 31, 2005, translation of abstract and substantial

(56) References Cited

OTHER PUBLICATIONS portions mentioned in the First Office Action dated Aug. 17, 2011, from SIPO for Chinese application No. 200880125611.1 (the Chinese counterpart of copending U.S. Appl. No. 12/238,105).
Jianping et al.,"Study on Feature Extraction of the Sleep-Multigraph", Journal of Biomedical Engineering, Issue 5, vol. 22, p. 906-909, Dec. 31, 2005, English translation of abstract only.
Office Action from Chinese application No. 200880125611.1 (the Chinese counterpart of copending U.S. Appl. No. 12/238,105), dated Aug. 17, 2011, 10 pp.
Lima et al., "The Role of the Substantia Nigra Pars Compacta in Regulating Sleep Patterns in Rats," PLoS One, www.plosone.org, Jun. 2007, Issue 6, e514 (7 pgs.).
Piette et al., "A unique episode of REM sleep behavior disorder triggered during surgery for Parkinson's disease," Journal of the Neurological Sciences 253 (2007) pp. 73-76.
Antonini et al., "Deep brain stimulation and its effect on sleep in Parkinson's disease," Sleep Medicine 5 (2004) pp. 211-214.
Foffani et al., "Analysis of local field potentials from the human subthalamic nucleus," Proceedings of the $25^{th}$ Annual International Conference of the IEEE EMBS, Cancun, Mexico, Sep. 17-21, 2003, pp. 2292-2294.
Takakusaki et al., "Evidence for a role of basal ganglia in the regulation of rapid eye movement sleep by electrical and chemical stimulation for the pedunculopontine tegmental nucleus and the substantia nigra pars reticulate in decerebrate cats," Neuroscience, 2004:124(1):207-20.
U.S. Appl. No. 12/238,105, filed Sep. 25, 2008 entitled "Sleep Stage Detections."
U.S. Appl. No. 60/999,096, filed Oct. 16, 2007 entitled "Device Control Based on Prospective Movement."
U.S. Appl. No. 60/999,097, filed Oct. 16, 2007 entitled "Responsive Therapy System."
Response to Office Action dated Oct. 10, 2012, from U.S. Appl. No. 12/238,105, filed Jan. 10, 2013, 25 pp.
Office Action for U.S. Appl. No. 12/238,105, mailed Oct. 10, 2012, 14 pages.
Response to Office Action dated Jan. 22, 2014, from U.S. Appl. No. 12/238,105, filed Apr. 22, 2014, 18 pp.
Final Office Action from U.S. Appl. No. 12/238,105, dated Jul. 2, 2014, 15 pp.
Office Action from U.S. Appl. No. 12/238,105, dated Jan. 22, 2014, 16 pp.
Amendment in Response to Office Action dated Jul. 2, 2014, from U.S. Appl. No. 12/238,105, filed Oct. 2, 2014, 19 pp.
Notice of Allowance from U.S. Appl. No. 12/238,105, dated Feb. 25, 2015, 10 pp.
Final Office Action from U.S. Appl. No. 12/238,105, dated Jun. 13, 2013, 17 pp.
Advisory Action from U.S. Appl. No. 12/238,105, dated Aug. 28, 2013, 5 pp.
Pre-Appeal Brief Request for Review and Notice of Appeal from U.S. Appl. No. 12/238,105, filed Sep. 13, 2013, 7 pp.
Final Office Action from U.S. Appl. No. 14/733,349, dated Dec. 27, 2016, 7 pages.
Aaron et al., "Horizons in Prosthesis Development for the Restoration of Limb Function," Journal of the American Academy of Orthopaedic Surgeons, vol. 14, No. 10, Sep. 2006, pp. S198-S204.
Abidi, "CMOS wireless transceivers: the new wave," IEEE Communications Magazine 37, Aug. 1999, pp. 119-124.
Academic Press Dictionary of Science and Technology, definition of "baseband" Oxford: Elsevier Science and Technology, 1992, 2 pp. (Applicant points out that, in accordance with MPEP 609.04(a), the 1992 year of publication is sufficiently earlier than the effective U.S. filing date and any foreign priority date so that the particular month of publication is not in issue.).
Acuna et al., "Cognitive mechanisms of transitive inference," Exp Brain Res, vol. 146, Sep. 2002, pp. 1-10.
Acuna et al., "Frontal and Parietal Lobe Activation during Transitive Inference in Humans," Cerebral Cortex, vol. 12, No. 12, Dec. 2002, pp. 1312-1321.
Anderson et al., "Recording Advances for Neural Prosthetics," Engineering in Medicine and Biology Society, IEMBS 2004, 26th Annual International Conference of the IEEE, vol. 7, Sep. 2004, pp. 5352-5355.
Anderson et al., "Selecting the signals for a brain-machine interface," Current Opinion Neurobiology, vol. 14, Dec. 2004, pp. 720-726.
Authoritative Dictionary of IEEE Standard Terms (Seventh Edition), definition of "baseband" pp. 86, New York: IEEE, 2000, 3 pp. (Applicant points out that, in accordance with MPEP 609.04(a), the 2000 year of publication is sufficiently earlier than the effective U.S. filing date and any foreign priority date so that the particular month of publication is not in issue.).
Avestruz et al., "A 5 uW/Channel Spectral Analysis IC for Chronic Bidirectional Brain-Machine Interfaces," IEEE Journal of Solid-State Circuits, vol. 43, No. 12, Dec. 2008, 19 pp.
Bakker et al., "A CMOS Nested-Chopper Instrumentation Amplifier with 100-nV Offset," IEEE Journal of Solid-State Circuits, vol. 35, No. 12, Dec. 2000, pp. 1877-1883.
Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pp.
Brown et al., "Basal ganglia local field potential activity: Character and functional significance in the human," Clinical Neurophysiology, vol. 116, Nov. 2005, pp. 2510-2519.
Brown, "Oscillatory Nature of Human Basal Ganglia Activity: Relationship to the Pathophysiology of Parkinson's Disease," Movement Disorders, vol. 18, No. 4, Apr. 2003, pp. 357-363.
Burt et al., "A Micropower Chopper-Stabilized Operational Amplifier using an SC Notch Filter with Synchronous Integration inside the Continuous-Time Signal Path," ISSCC Digest of Technical Papers 2006, Paper 19.6, Feb. 2006, 2 pp.
Cohen et al., "The physiology of brain-computer interfaces," Journal of Physiology, vol. 579, No. 3, Mar. 2007, p. 570.
Denison et al., "A 2 µW 100 nV/rtHz Chopper-Stabilized Instrumentation Amplifier for Chronic Measurement of Neural Field Potentials," Solid-state circuits, IEEE Journal, vol. 42, Dec. 2007, pp. 2934-2945.
Denison et al., "A 2.2µW 94 nV/vHz, Chopper-Stabilized Instrumentation Amplifier for EEG Detection in Chronic Implants," Solid-State Circuits Conference, Digest of Technical Papers, IEEE International, Feb. 2007, 3 pp.
Denison et al., "An 8 µW heterodyning chopper amplifier for direct extraction of 2 µVrms Neuronal Brain Biomarkers," ISSCC, Paper 8.1, Feb. 2008, 3 pp.
Donoghue et al., "Assistive technology and robotic control using motor cortex ensemble-based neural interface systems in humans with tetraplegia," Journal of Physiology 579.3, Mar. 2007, pp. 603-611.
Donoghue et al., "Development of neuromotor prostheses for humans," Advances in Clinical Neurophysiology, Supplements to Clinical Neurophysiology, vol. 57, 2004, pp. 592-606 (Applicant points out that, in accordance with MPEP 609.04(a), the 2004 year of publication is sufficiently earlier than the effective U.S. filing date and any foreign priority date so that the particular month of publication is not in issue.).
Donoghue et al., "Motor Areas of the Cerebral Cortex," Journal of Clinical Neurophysiology, vol. 11, No. 4, Jul. 1994, pp. 382-396.
Donoghue, "Connecting cortex to machines: recent advances in brain interfaces," Nature Neuroscience, supplement, vol. 5, Nov. 2002, pp. 1085-1088.
Dzwonczyk et al., "Myocardial Electrical Impedance Responds to Ischemia and Reperfusion in Humans," IEEE Transactions on Biomedical Engineering, IEEE Service Center, vol. 51, No. 12, Dec. 2004, pp. 2206-2209.
Eden et al., "Reconstruction of Hand Movement Trajectories from a Dynamic Ensemble of Spiking Motor Cortical Neurons," Pro-

(56) References Cited

OTHER PUBLICATIONS ceedings of the 26th Annual International Conference of the IEEE EMBS, San Francisco, CA, USA, Sep. 1-5, 2004, pp. 4017-4020.
Enz et al., "Circuit Techniques for Reducing the Effects of Opamp Imperfections," Proceedings of the IEEE, vol. 84, No. 11, Nov. 1996, pp. 1584-1614.
Fetz, "Volitional control of neural activity: implications for brain-computer interfaces," Journal of Physiology, vol. 579, No. 3, Mar. 2007, pp. 571-579.
Friehs et al., "Brain-Machine and Brain-Computer Interfaces," Stroke, vol. 35, No. 11, Supplement 1, Nov. 2004, pp. 2702-2705.
Haddad et al., "An ultra-low-power dynamic translinear cardiac sense amplifier for pacemakers," Circuits and Systems, vol. 5, Mar. 2003, pp. V-37-V40.
Haddad et al., "Analog wavelet transform employing dynamic translinear circuits for cardiac signal characterization," Circuits and Systems, vol. 1, May 2003, pp. 1-121-1-124.
Hadiashar et al., "A Chopper Stabilized CMOS Analog Multiplier with Ultra Low DC Offsets," Solid-State Circuits Conference, Sep. 2006, pp. 364-367.
Harrison et al., "A Low-Power Integrated Circuit for a Wireless 100 — Electrode Neural Recording System," IEEE Journal of Solid State Circuits, vol. 42, No. 1, Jan. 2007, pp. 123-133.
Harrison et al., "A Low-Power Low-Noise CMOS Amplifier for Neural Recording Applications," IEEE Journal of Solid-State Circuits, vol. 38, No. 6, Jun. 2003, pp. 958-965.
Harrison et al., "Local Field Potential Measurement with Low-Power Analog Integrated Circuit," Proceedings of the 26th Annual International Conference of the IEEE EMBS, Sep. 1-5, 2004, 4 pp.
Hatsopoulos et al., "Cortically controlled brain-machine interface," Proceedings of the 2005 IEEE, Engineering in Medicine and Biology 27th Annual Conference, Sep. 1-4, 2005, pp. 7660-7663.
Heldman et al., "Local Field Potential Spectral Tuning in Motor Cortex During Reaching," IEEE Transactions on Neural Systems and Rehabilitation Engineering, vol. 14, No. 2, Jun. 2006, pp. 180-183.
Hess et al., "Long-Term Potentiation of Horizontal Connections Provides a Mechanism to Reorganize Cortical Motor Maps," Journal of Neurophysiology, vol. 71, No. 6, Jun. 1994, pp. 2543-2547.
Hochberg et al., "Neuronal ensemble control of prosthetic devices by a human with tetraplegia," Nature, vol. 442, Jul. 2006, pp. 164-171.
Hochberg et al., "Sensors for Brain-Computer Interfaces: Options for Turning Thought into Action," IEEE Engineering in Medicine and Biology Magazine, Sep./Oct. 2006, pp. 32-38.
Hoshi," Functional specialization within the dorsolateral prefrontal cortex: A review of anatomical and physiological studies of non-human primates," Neuroscience Research 54, Feb. 2006, pp. 73-84.
Krusienski et al.,"A μ— Rhythm Matched Filter for Continuous Control of a Brain-Computer Interface," IEEE Transactions on Biomedical Engineering, vol. 54, Feb. 2007, pp. 273-280.
Kun et al., "Algorithm for Tissue Ischemia Estimation Based on Electrical Impedance Spectroscopy," IEEE Transactions on Biomedical Engineering, IEEE Service Center, vol. 50, No. 12, Dec. 2003, pp. 1352-1359.
Lai et al. "Muscle Tone Suppression and Stepping Produced by Stimulation of Midbrain and Rostral Pontine Reticular Formation," the Journal of Neuroscience, vol. 10, No. 8, Aug. 1990, 8 pp.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Mar. 2008, pp. 76-77.
Makinwa et al., "A CMOS Temperature-to-frequency converter with an Inaccuracy of less than ±0.5 °C (3σ) from -40 °C to 105 °C," IEEE Journal of Solid State Circuits, vol. 41, No. 12, Dec. 2006, pp. 2992-2997.
Makinwa, "Dynamic Offset Cancellation Techniques," Smart Sensor Systems '02, May 2002, 42 pp.

Martins et al., "A CMOS IC for Portable EEG Acquisition Systems," IEEE Transactions on Instrumentation and Measurement, vol. 47, No. 5, Oct. 1998, pp. 1191-1196.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 2007, 5 pp.
Maynard et al., "Neuronal Interactions Improve Cortical Population Coding of Movement Direction," The Journal of Neuroscience, vol. 19, No. 18, Sep. 15, 1999, pp. 8083-8093.
Min et al., "Electrical Impedance and Cardiac Monitoring— Technology, Potential and Applications," International Journal of Bioelectromagnetism, International Society for Bioelectromagnetism, vol. 5, No. 1, Jan. 2003, pp. 53-56.
Neagu et al. "PPN Evoked Potentials During STN Stimulation of Parkinson's Disease Patients," Presentation Abstract, 40th Annual Meeting Neuroscience, Nov. 16, 2010, 2 pp.
Ng et al., "A CMOS Analog Front-End IC for Portable EEG/ECG Monitoring Applications," IEEE Trans. On Circuits and Systems, vol. 52, No. 11, Nov. 2005, 13 pp.
Ojakangas et al, "Decoding movement intent from human premotor cortex neurons for neural prosthetic applications," Journal of Clinical Neurophysiology, vol. 23, No. 6, Dec. 2006, pp. 1-14.
Paninski et al., "Spatiotemporal Tuning of Motor Cortical Neurons for Hand Position and Velocity," Journal of Neurophysiology, vol. 91, Jan. 2004, pp. 515-532.
Paninski et al., "Superlinear Population Encoding of Dynamic Hand Trajectory in Primary Motor Cortex," The Journal of Neuroscience, vol. 24, No. 39, Sep. 29, 2004, pp. 8551-8561.
Patterson et al., "A Microelectrode/Microelectronic Hybrid Device for Brain Implantable Neuroprosthesis Applications," IEEE Transactions on Biomedical Engineering, vol. 51, No. 10, Oct. 2004, pp. 1845-1853.
Rauscher et al., "Practical Realization of an Analyzer Operating on the Heterodyne Principle," Chapter 4 (partial) of Fundamentals of Spectrum Analysis, Rohde & Schwarz, 2001, pp. 34-64 (Applicant points out that, in accordance with MPEP 609.04(a), the 2001 year of publication is sufficiently earlier than the effective U.S. filed and any foreign priority date so that the particular month of publication is not in issue.).
Rudell et al. "Recent Developments in High Integration Multi-Standard CMOS Transceivers for Personal Communication Systems," 1998 International Symposium on Low Power Electronics and Design, Aug. 1998, pp. 149-154.
Salthouse et al., "A practical micropower programmable bandpass filter for use in bionic ears," Solid-state Circuits, IEEE Journal, vol. 38, Jan. 2003, pp. 63-70.
Sanduleanu et al., "A Low Noise, Low Residual Offset, Chopped Amplifier for Mixed Level Applications," IEEE, 0-7803-5008-1/98, Sep. 1998, pp. 333-336.
Sanes et al., "Plasticity and Primary Motor Cortex," Annual Review of Neuroscience, vol. 23, Mar. 2000, pp. 393-415.
Sarpeshkar et al., "An ultra-low-power programmable analog bionic ear processor," Biomedical Engineering, IEEE Transactions, vol. 52, Apr. 2005, pp. 711-727.
Sarpeshkar et al., "Low power circuits for brain — machine interfaces," IEEE Transactions on Biomedical Circuits and Systems, vol. 2, No. 3, Sep. 2008, pp. 173-183.
Sarpeshkar, "Borrowing from biology makes for low-power computing," IEEE Spectrum, May 2006, pp. 24-29.
Schwartz, "Useful signals from motor cortex", Journal of Physiology, vol. 579, No. 3, Mar. 2007, pp. 581-601.
Serruya et al., "Instant neural control of a movement signal," Nature, vol. 416, Mar. 2002, pp. 141-142.
Serruya et al., "Robustness of neuroprosthetic decoding algorithms," Biological Cybernetics, vol. 88, Feb. 2003, pp. 219-228.
Shoham et al., "Statistical Encoding Model for a Primary Motor Cortical Brain-Machine Interface," IEEE Transactions on Biomedical Engineering, vol. 52, No. 7, Jul. 2005, pp. 1312-1322.
Silberstein et al., "Patterning of globus pallidus local field potentials differs between Parkinson's disease and dystonia," Brain, vol. 126, Aug. 2003, pp. 2597-2608.

(56) References Cited

OTHER PUBLICATIONS

Smart et al., "Automatic Detection of High Frequency Epileptiform Oscillations from Intracranial EEG Recordings of Patients with Neocortical Epilepsy," Technical, Professional and Student Development Workshop, IEEE Region 5 and IEEE Denver Section, Apr. 2005, pp. 53-58.

Song et al., "Development of a Chipscale Integrated Microelectrode/Microelectronic Device for Brain Implantable Neuroengineering Applications," IEEE Transactions on Neural Systems and Rehabilitation Engineering, vol. 13, No. 2, Jun. 2005, pp. 220-226.

Song et al., "Development of an Integrated Microelectrode/Microelectronic Device for Brain Implantable Neuroengineering Applications," Proceedings of the 26th Annual International Conference of the IEEE EMBS, San Francisco, CA, USA, Sep. 1-5, 2004, pp. 4053-4056.

Suner et al., "Reliability of Signals from a Chronically Implanted, Silicon-Based Electrode Array in Non-Human Primate Primary Motor Cortex," IEEE Transactions on Neural Systems and Rehabilitation Engineering, vol. 13, No. 4, Dec. 2005, pp. 524-541.

Tornqvist et al., "Effects of Different Electrical Parameter Settings on the Intelligibility of Speech in Patients with Parkinson's Disease Treated with Subthalamic Deep Brain Stimulation," Movement Disorders, vol. 20, No. 4, Apr. 2005, pp. 416-423.

Wattanapanitch et al., "An energy-efficient micropower neural recording amplifier," Biomedical Circuits and Systems, IEEE Transactions, vol. 1, Jun. 2007, pp. 136-147.

Wingeier et al., "Intra-operative STN DBS attenuates the prominent beta rhythm in the STN in Parkinson's disease," Experimental Neurology, Nov. 2005, 8 pp.

Wolpaw, "Brain-computer interfaces as new brain output pathways," Journal of Physiology, vol. 579, No. 3, Jan. 2007, pp. 613-619.

Wood et al., "Automatic Spike Sorting for Neural Decoding," Proceedings of the 26th Annual International Conference of the IEEE EMBS, San Francisco, CA, USA, Sep. 1-5, 2004, pp. 4009-4012.

Wood et al., "Inferring Attentional State and Kinematics from Motor Cortical Firing Rates," Proceedings of the 2005 IEEE, Engineering in Medicine and Biology 27th Annual Conference, Sep. 1-4, 2005, pp. 149-152.

Wood et al., "On the Variability of Manual Spike Sorting," IEEE Transactions on Biomedical Engineering, vol. 51, No. 6, Jun. 2004, pp. 912-918.

Wu et al., "A 1V 2.3µW Biomedical Signal Acquisition IC," ISSCC Digest of Technical Papers 2006, paper 2.7, Feb. 2006, 2 pp.

Wu et al., "Bayesian Population Decoding of Motor Cortical Activity Using a Kalman Filter," Neural Computation, vol. 18, No. 1, Jan. 2006, pp. 80-118.

Wu et al., "Closed-Loop Neural Control of Cursor Motion using a Kalman Filter," Proceedings of the 26th Annual International Conference of the IEEE EMBS, San Francisco, CA, USA, Sep. 1-5, 2004, pp. 4126-4129.

Wu et al., "Modeling and Decoding Motor Cortical Activity Using a Switching Kalman Filter," IEEE Transactions on Biomedical Engineering, vol. 51, No. 6, Jun. 2004, pp. 933-942.

Yates et al., "An ultra-low power low noise chopper amplifier for wireless EEG," In 49th IEEE International Midwest Symposium on Circuits and Systems, MWSCAS '06, vol. 2, Jan. 2006, pp. 449-452.

Yazicioglu et al., "A 200µW Eight-Channel Acquisition ASIC for Ambulatory EEG Systems," Solid-state circuits conference, Jul. 2008, 3 pp.

Yazicioglu et al., "A 60 µW 60nV/ √Hz Readout Front-End for Portable Biopotential Acquisition Systems," ISSCC Digest of Technical Papers 2006, paper 2.6, Feb. 2006, 2 pp.

Ying, "Chopper Stabilized Amplifiers," Term Paper, Department of Electrical and Computer Engineering, University of Toronto, Nov. 12, 2001, 17 pp.

Urrestarazu et al., "Beta Activity in the Subthalamic Nucleus During Sleep in Patients with Parkinson's Disease," Movement Disorders, vol. 24, Issue No. 2, published online Oct. 24, 2008, (pp. 254-260).

Prosecution History from U.S. Appl. No. 12/238,105, dated Jan. 26, 2012 through Jun. 8, 2015, 228 pp.

Prosecution History from U.S. Appl. No. 14/733,349, dated Aug. 3, 2016 through Mar. 14, 2017, 62 pp.

International Preliminary Report on Patentability from International Application No. PCT/US2010/055943, dated May 15, 2012, 7 pp.

* cited by examiner

DEEP BRAIN STIMULATION FOR SLEEP AND MOVEMENT DISORDERS

TECHNICAL FIELD

The disclosure relates to medical therapy systems, and, more particularly, control of medical therapy systems.

BACKGROUND

In some cases, an ailment or medical condition may affect the quality of a patient's sleep. For example, neurological disorders may cause a patient to have difficulty falling asleep, and may disturb the patient's sleep, e.g., cause the patient to wake frequently during the night and/or early in the morning. Further, neurological disorders may cause the patient to have difficulty achieving deep sleep stages, such as one or more of the nonrapid eye movement (NREM) sleep stages.

Examples of neurological disorders that may negatively affect patient sleep quality include movement disorders, such as tremor, Parkinson's disease, multiple sclerosis, or spasticity. The uncontrolled movements associated with such movement disorders may cause a patient to have difficulty falling asleep, disturb the patient's sleep, or cause the patient to have difficulty achieving deep sleep stages. Parkinson's disease may also cause rapid eye movement (sleep) behavior disorders (RBD), in which case, a patient may act out dramatic and/or violent dreams, shout or make other noises (e.g., grunting) during the rapid eye movement (REM) stage sleep.

Drugs are often used to treat neurological disorders. In some cases, neurological disorders are treated via an implantable medical device (IMD), such as an implantable stimulator or drug delivery device. The treatments for neurological disorders may themselves affect sleep quality. Further, in some cases, poor sleep quality may increase the symptoms experienced by a patient. For example, poor sleep quality may result in increased movement disorder symptoms in movement disorder patients. The link between poor sleep quality and increased symptoms is not limited to ailments that negatively impact sleep quality, such as those listed above. Nonetheless, the condition of a patient with such an ailment may progressively worsen when symptoms disturb sleep quality, which may, in turn, increase the frequency and/or intensity of symptoms of the patient's condition.

SUMMARY

In general, the disclosure is directed to controlling an electrical stimulation device to deliver electrical stimulation to the substantia nigra and the subthalamic nucleus of a brain of a patient in order to treat a sleep disorder and a movement disorder of the patient. In some examples, during a sleep state of the patient, a sleep stage of the patient is determined and an electrical stimulation device is controlled to deliver of stimulation to one or both of the substantia nigra and the subthalamic nucleus based on the determined sleep stage. Independently controlling the delivery of stimulation to the substantia nigra and the subthalamic nucleus helps separately address the sleep disorder and movement disorder symptoms that are observed during specific sleep stages of a sleep state.

In one aspect, the disclosure is directed to a method comprising determining a sleep stage of a patient, controlling an electrical stimulation device to deliver electrical stimulation to a substantia nigra of the patient based on the determined sleep stage, and controlling the electrical stimulation device to deliver electrical stimulation to a subthalamic nucleus of the patient based on the determined sleep stage. Delivery of electrical stimulation to the substantia nigra and delivery of electrical stimulation to the subthalamic nucleus are independently controlled.

In another aspect, the disclosure is directed to a system comprising an electrical stimulation device and a processor that determines a sleep stage of a patient, controls the electrical stimulation device to deliver electrical stimulation to a substantia nigra of the patient based on the determined sleep stage, and controls the electrical stimulation device to deliver electrical stimulation to a subthalamic nucleus of the patient based on the determined sleep stage of the patient. The processor independently controls delivery of electrical stimulation to the substantia nigra and delivery of electrical stimulation to the subthalamic nucleus.

In another aspect, the disclosure is directed to a computer-readable storage medium comprising instructions. The instructions cause a programmable processor to determine a sleep stage of a patient based on a brain signal sensed within a brain of the patient, control an electrical stimulation device to deliver electrical stimulation to a substantia nigra of the brain of the patient based on the determined sleep stage, and control the electrical stimulation device to deliver electrical stimulation to a subthalamic nucleus of the brain of the patient based on the determined sleep stage of the patient. The instructions cause the programmable processor to independently control the electrical stimulation to deliver stimulation to the substantia nigra and the subthalamic nucleus.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of the disclosure are set forth in the accompanying drawings and the description below. Other features, objects, and advantages of the systems, methods, and devices in accordance with the disclosure will be apparent from the description and drawings, and from the claims.

DETAILED DESCRIPTION

Figure 1:
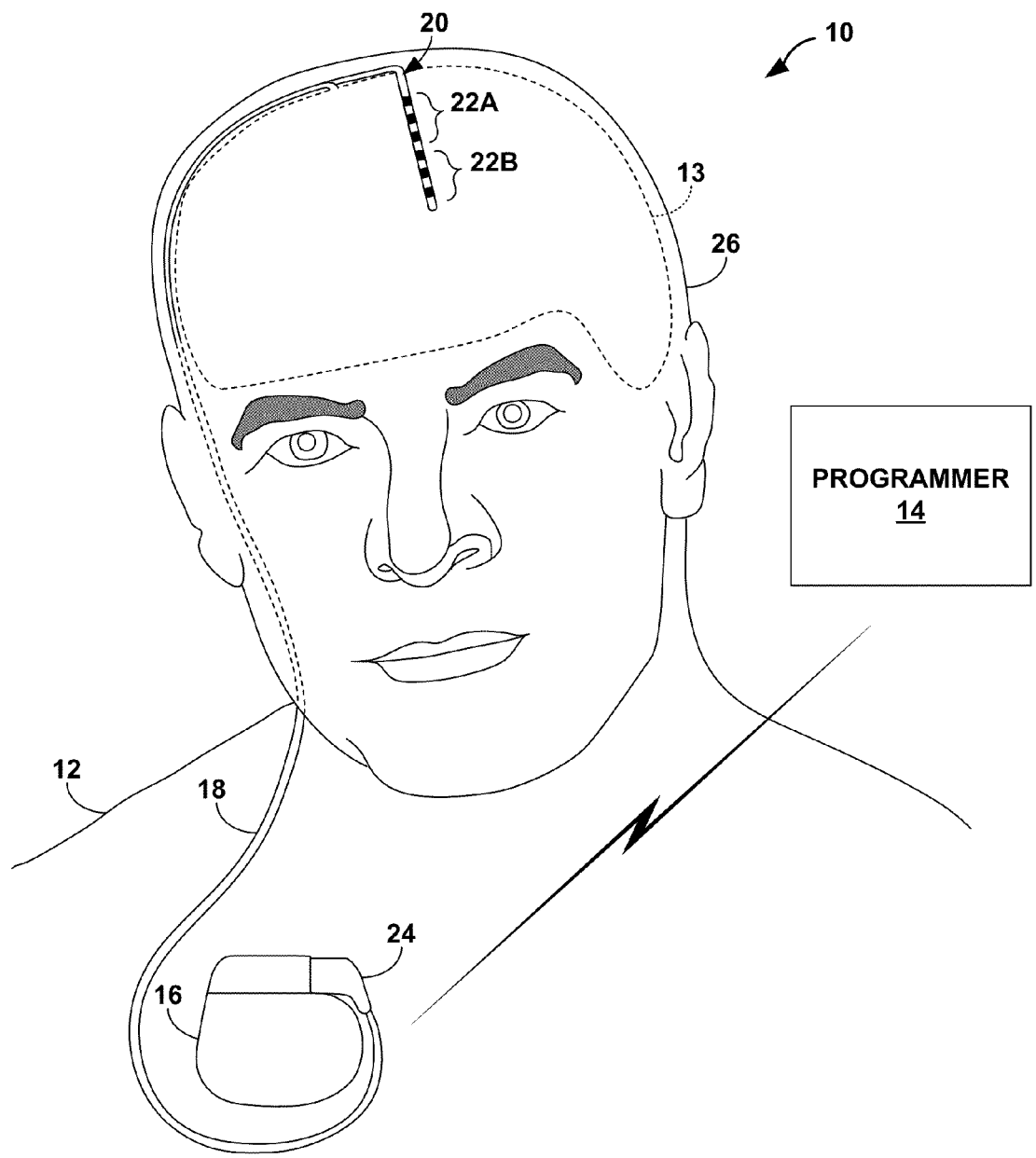
FIG. 1 is a conceptual diagram illustrating an example deep brain stimulation (DBS) system.

In some cases, a patient's ability to sleep or quality of sleep is affected by symptoms of a movement disorder. Delivery of electrical stimulation to the subthalamic nucleus of a patient may help manage symptoms of the movement disorder of the patient, and, in some cases, the electrical stimulation of the subthalamic nucleus may also help to manage a sleep disorder of the patient, where the sleep disorder may or may not be related to the movement disorder. However, in some cases, electrical stimulation of the subthalamic nucleus may not be sufficient to manage the sleep disorder. Electrical stimulation of the substantia nigra (e.g., the substantia nigra pars reticulata and/or the substantia nigra pars compacta) of the brain of the patient may more directly target symptoms associated with a sleep disorder of the patient than electrical stimulation of the subthalamic nucleus. In some cases, the movement and sleep disorders may result from the same patient condition (e.g., Parkinson's disease) or, in other cases, the movement and sleep disorders may be unrelated. In either case, it may be advantageous to electrically stimulate both the subthalamic nucleus and the substantia nigra of the patient with the same therapy system. Therapy delivered to the subthalamic nucleus may more directly target symptoms associated with the movement disorder, while therapy delivered to the substantia nigra may more directly target symptoms associated with the sleep disorder.

According to techniques described herein, therapy delivery to the subthalamic nucleus and/or to the substantia nigra of a patient is controlled based on a determined sleep state or sleep stage of the patient. Controlling the electrical stimulation device may include activating electrical stimulation, deactivating electrical stimulation, increasing an intensity of electrical stimulation, or decreasing an intensity of electrical stimulation based on the determined sleep stage. Intensity of stimulation may be a function of, for example, any one or more of the voltage or current amplitude value of the stimulation signal, frequency of stimulation signals, signal duration (e.g., pulse width in the case of stimulation pulses), signal burst pattern, and the like. The intensity of stimulation may, for example, affect the volume of tissue that is activated by the electrical stimulation.

In accordance with the disclosure, therapy delivery to the subthalamic nucleus and the substantia nigra are independently controlled, such that stimulation delivered to the subthalamic nucleus may occur at a different time and based on different control parameters (e.g., different sleep stages or brain signals) than therapy delivery to the substantia nigra. In this way, the target tissue site (e.g., the substantia nigra or the subthalamic nucleus) for stimulation therapy can be selected to better address patient symptoms, some of which may be observed during one sleep stage, but not another sleep stage.

A sleep stage of a patient may be determined based on a biosignal that is indicative of activity within the brain of the patient. Examples of biosignals indicative of activity within a brain of a patient include, but are not limited to, bioelectrical brain signals, such as electrical signals generated from local field potentials within one or more regions of brain 13, such as, but not limited to, an electroencephalogram (EEG) signal or an electrocorticogram (ECoG) signal. In some examples, the electrical signals within the brain of the patient may reflect changes in electrical current produced by the sum of electrical potential differences across brain tissue.

In some examples, the electrical stimulation device may be controlled to deliver electrical stimulation to the substantia nigra and the subthalamic nucleus via different electrodes of a single lead of the electrical stimulation device or via different electrodes of two or more leads, where the electrodes are positioned to independently stimulate the substantia nigra and the subthalamic nucleus. That is, the different electrodes of the one or more leads can be arranged to deliver stimulation to only one of the substantial nigra or the subthalamic nucleus at a time, or, if desired, both the substantial nigra at the subthalamic nucleus. As discussed above, delivery of electrical stimulation to the substantia nigra and delivery of electrical stimulation to the subthalamic nucleus may be independently controlled. As a result, in some cases, stimulation is delivered to the substantia nigra and not the subthalamic nucleus, while in other cases, stimulation is delivered to the subthalamic nucleus and not the substantia nigra. In addition, in some cases, stimulation is delivered to both the substantia nigra and not the subthalamic nucleus.

In some examples, electrical stimulation may be delivered to the substantia nigra of a patient according to a first therapy program and to the subthalamic nucleus of the patient according to a second therapy program that defines at least one stimulation parameter that is different than the first therapy program. Electrical stimulation therapy according to the first and second therapy programs may be delivered independently, simultaneously, and/or alternatively. In some examples, the first and second therapy programs may be selected or modified based on the determined sleep stage of the patient or the first and second therapy programs may be modified based on the determined sleep stage.

As described in further detail below with respect to FIG. 9, at least a part of a lead can be implanted within a patient, and the location of the electrodes of the lead within the patient can be determined based on analysis of a biosignal of the patient sensed via the electrodes. For example, a particular physiological structure of the patient (e.g. the substantia nigra) may exhibit a unique biosignal and, thus, facilitate positioning of the electrodes of the lead at the desired implant location (e.g., near the target tissue) through monitoring of the biosignal.

FIG. 1 is a conceptual diagram illustrating an example deep brain stimulation (DBS) system 10 that manages a medical condition of patient 12, such as a neurological disorder. DBS system 10 includes medical device programmer 14, implantable medical device (IMD) 16, lead extension 18, and lead 20 with respective electrodes 22A and 22B (collectively referred to as "electrodes 22"). Patient 12 ordinarily will be a human patient. In some cases, however, DBS system 10 may be applied to other mammalian or non-mammalian non-human patients. As previously mentioned, some patient conditions, such as Parkinson's disease and other neurological conditions, result in impaired sleep states. DBS system 10 may provide therapy in order to minimize the severity or duration of the patient condition, and, in some cases, in order to eliminate symptoms associated with the patient condition, including impaired sleep states.

In the example shown in FIG. 1, DBS system 10 includes a processor that determines whether patient 12 is in a sleep state, and controls delivery of electrical stimulation to patient 12 upon determining that patient 12 is in the sleep state. The sleep state may refer to a state in which patient 12 is intending on sleeping (e.g., initiating thoughts of sleep), is attempting to sleep, or has initiated sleep and is currently sleeping. In addition, the processor may determine a sleep stage of the sleep state based on a biosignal detected within brain 13 of patient 12, and may control delivery of electrical stimulation to patient 12 based on a determined sleep stage.

Within a sleep state, patient 12 may be within one of a plurality of sleep stages. Example sleep stages include Stage 1 (also referred to as Stage N1 or S1), Stage 2 (also referred to as Stage N2 or S2), Deep Sleep (also referred to as slow wave sleep), and rapid eye movement (REM). The Deep Sleep sleep stage may include multiple sleep stages, such as Stage N3 (also referred to as Stage S3) and Stage N4 (also referred to as Stage S4). In some cases, patient 12 may cycle through the Stage 1, Stage 2, Deep Sleep, and REM sleep stages more than once during a sleep state. The Stage 1, Stage 2, and Deep Sleep sleep stages may be considered non-REM (NREM) sleep stages.

During the Stage 1 sleep stage, patient 12 may be in the beginning stages of sleep, and may begin to lose conscious awareness of the external environment. During the Stage 2 and Deep Sleep sleep stages, muscular activity of patient 12 may decrease, and conscious awareness of the external environment may disappear. During the REM sleep stage, patient 12 may exhibit relatively increased heart rate and respiration compared to the Stage 1, Stage 2, and Deep Sleep sleep stages. In some cases, the Stage 1, Stage 2, and Deep Sleep sleep stages may each last about five minutes to about fifteen minutes, although the actual time ranges may vary between patients. In some cases, REM sleep may begin about ninety minutes after the onset of sleep, and may last about five minutes to about fifteen minutes or more, although the actual time ranges may vary between patients.

In some examples, a processor of DBS system 10 (e.g., a processor of programmer 14 or IMD 16) controls delivery of electrical stimulation by activating electrical stimulation, deactivating electrical stimulation, increasing the intensity of electrical stimulation, or decreasing the intensity of electrical stimulation delivered to patient 12 (while still delivering some electrical stimulation) based on the determined sleep stage. In addition, DBS system 10 may select a target tissue site (e.g., a target structure within brain 13) for the electrical stimulation based on the determined sleep stage. As discussed in further detail below, in some examples, DBS system 10 delivers stimulation to one or both of the substantia nigra and the subthalamic nucleus of brain 13 based on a determined sleep stage of patient 12.

DBS system 10 may also store a plurality of therapy programs (e.g., a set of electrical stimulation parameter values), and at least one stored therapy program may be associated with at least one sleep stage and/or a target tissue site (e.g., the subthalamic nucleus and the substantia nigra). A processor of IMD 16 or programmer 14 may select a stored therapy program that defines electrical stimulation parameter values for delivery of electrical stimulation to patient 12 based on a determined sleep stage and, in some cases, based on a selected target tissue site. In this way, the processor may control delivery of electrical stimulation to patient 12 based on the determined sleep stage. In some examples, at least one of the stored therapy programs is associated with a respective one of at least two different sleep stages. In addition, in some examples, at least one of the stored therapy programs is associated with at least two different sleep stages.

DBS system 10 is useful for managing a patient condition that results in an impaired sleep state, which may be identified by impaired sleep quality in one or more sleep stages. Different electrical stimulation parameter values may provide efficacious therapy (e.g., improved sleep quality) for different sleep stages of patient 12. In addition, different target tissue sites within brain 13 can provide efficacious therapy for different sleep stages of patient 12. Rather than delivering electrical stimulation regardless of the patient's current sleep stage, DBS system 10 selectively controls delivery of electrical stimulation according to different therapy programs and different target tissue sites (e.g., the subthalamic nucleus and the substantia nigra) in order to provide efficacious therapy during a determined sleep stage of patient 12. Further, in some examples, delivery of electrical stimulation to patient 12 may be decreased or deactivated upon determining a particular sleep stage, thereby conserving power of IMD 16, which may have a limited amount of stored power.

In other examples, DBS system 10 may modify at least one electrical stimulation parameter value of a stored therapy program (e.g., a set of therapy parameter values) based on a determined sleep stage. The modifications to the therapy program may be made based on stored instructions that are associated with the determined sleep stage. The modifications to the therapy program may include modifications that activate electrical stimulation to one or more target tissue sits (e.g., the subthalamic nucleus or the substantia nigra), deactivate electrical stimulation, increase an intensity of electrical stimulation, or decrease an intensity of electrical stimulation based on the determined sleep stage.

The modifications to the therapy program may also help IMD 16 deliver electrical stimulation to different target tissue sites (e.g., brain structures) within brain 13. For example, different electrode combinations or different intensities of stimulation (e.g., as indicated by stimulation signal characteristics such as voltage or current amplitude, frequency, and pulse width) may direct electrical stimulation to different regions within brain 13. As described in further detail below, the therapeutic effects of electrical stimulation can change depending on the region of brain 13 to which the stimulation is delivered, and the therapeutic effects of the stimulation therapy may be selected based on the detected sleep stage of patient 12. In this way, DBS system 10 is configured to adapt electrical stimulation to a current sleep stage and deliver responsive therapy during the sleep stage. The current sleep stage may be the sleep stage of patient 12 at approximately the same time at which the sleep stage is determined and, in some cases, approximately the same time at which a therapy program is selected.

As previously discussed, a sleep stage may refer to a particular phase of sleep during a sleep state of patient 12, whereas the sleep state refers to a situation in which patient 12 is intending on sleeping (e.g., initiating thoughts of sleep), is attempting to sleep or has initiated sleep and is currently sleeping. When patient 12 attempts to sleep, patient 12 may successfully initiate sleep, but may not be able to maintain a certain sleep stage (e.g., a Deep Sleep sleep stage). As another example, when patient 12 attempts to sleep, patient 12 may not be able to initiate sleep or may not be able to initiate a certain sleep stage.

In some cases, a patient condition, such as Parkinson's disease, may affect the quality of a patient's sleep. For example, patients that are afflicted with neurological disorders may suffer from sleep disturbances, such as insomnia, disturbances in REM sleep (e.g., REM sleep behavior disorders), disrupted sleep architecture, periodic limb movements or sleep respiratory disorders or daytime somnolence. Daytime somnolence may include excessive sleepiness caused by a decreased quality of sleep during the night. Accordingly, neurological disorders may cause patient 12 to have difficulty falling asleep and/or may disturb the sleep of patient 12, e.g., may cause patient 12 to wake periodically. Further, neurological disorders may cause patient 12 to have difficulty achieving deeper sleep stages, such as one or more of the NREM sleep stages. The sleep disorder symptoms may be related to nocturnal rigidity, hypokinesia, pain, effects of antiparkinsonian drugs, anxiety and depression (which may coexist with the movement disorder), and dysfunctions of one or more brain structures involved in sleep regulation.

Epilepsy is an example of a neurological disorder that may affect sleep quality. Other neurological disorders that may negatively affect patient sleep quality include movement disorders, such as tremor, Parkinson's disease, multiple sclerosis, or spasticity. Movement disorders may include symptoms such as rigidity, bradykinesia (i.e., slow physical movement), rhythmic hyperkinesia (e.g., tremor), nonrhythmic hyperkinsesia (e.g., tics) or akinesia (i.e., a loss of physical movement). Uncontrolled movements associated with some movement disorders or difficulty moving may cause a patient to have difficulty falling asleep, disturb the patient's sleep, or cause the patient to have difficulty achieving deeper sleep. Further, in some cases, poor sleep quality may increase the frequency or intensity of symptoms experienced by patient 12 due to a neurological disorder. For example, poor sleep quality has been linked to increased movement disorder symptoms in movement disorder patients.

In some examples, DBS system 10 or other types of therapy systems may help to manage sleep disorder symptoms of patients with conditions other than neurological conditions, such as psychiatric (or psychological) disorders. Examples of psychiatric disorders that may result in one or more impaired sleep stages include major depressive disorder, anxiety, hypomania or bipolar disorder.

In some examples, delivery of stimulation to one or more regions of brain 13, such as the subthalamic nucleus, may be an effective treatment for movement disorders, such as Parkinson's disease, and the treatment for the movement disorder may also improve sleep quality in certain aspects, e.g., by decreasing sleep fragmentation. Patient 12 may also have a sleep disorder that may or may not be related to the movement disorder. While the DBS provided to manage symptoms of the patient's movement disorder may help improve sleep quality, other aspects of the patient's sleep disorder may remain unimproved by the DBS to treat movement disorders. DBS system 10 delivers electrical stimulation therapy that helps mitigate symptoms associated with both the movement disorder and the sleep disorder, which may or may not be related to the movement disorder. In particular, DBS system 10 controls delivery of electrical stimulation to patient 12 based on a detected sleep stage, where the electrical stimulation delivery may be specifically configured to address sleep disorder symptoms associated with the detected sleep stage, in order to help alleviate at least some sleep disturbances associated with the movement disorder (e.g., sleep disorder symptoms associated with movement control) and sleep disturbances associated with the sleep disorder (e.g., sleep disorder symptoms associated with sleep regulation). Dynamically changing the electrical stimulation parameter values based on the patient's sleep stage may be useful for addressing the patient's sleep disorder symptoms in a more efficient and symptom-specific manner.

DBS system 10 also delivers stimulation to certain regions of brain 13, such as the substantia nigra, during a sleep stage in order to help patient 12 fall asleep, maintain the sleep stage or maintain deeper sleep stages (e.g., REM sleep). The electrical stimulation delivery sites for delivery of electrical stimulation during one or more sleep stages of patient 12 may be the same as or different from the electrical stimulation delivery sites used to deliver therapy to patient 12 to manage the patient's other condition (e.g., difficulty moving caused by a movement disorder). In addition to electrical stimulation therapy, a suitable pharmaceutical agent, such as acetylcholine, dopamine, epinephrine, norepinephrine, serotonine, inhibitors of noradrenaline or any agent for affecting a sleep disorder or combinations thereof may be delivered to patient 12 (e.g., delivered to brain 13 or another region within patient 12). By alleviating the patient's sleep disturbances and improving the quality of the patient's sleep, patient 12 may feel more rested, and, as a result, DBS system 10 may help improve the quality of the patient's life.

The substantia nigra of brain 13 may play a role in sleep regulation and the subthalamic nucleus of brain 13 may play a role in movement control. As also discussed with respect to FIG. 5, electrodes 22 of lead 20 may be positioned within brain 13 such that electrodes 22A deliver electrical stimulation to the subthalamic nucleus in order to effectively treat sleep disorder symptoms associated with movement control and electrodes 22B deliver electrical stimulation to the substantia nigra in order to effectively treat sleep disorder symptoms associated with sleep regulation. Delivery of electrical stimulation through electrodes 22A may also effectively treat symptoms associated with a movement disorder of patient 12 while patient 12 is in either of a sleep state or an awake state.

Patients with Parkinson's disease or other neurological disorders may have a poor quality of sleep associated with difficulty regulating sleep. Delivery of electrical stimulation to one or more regions of brain 13 may be an effective treatment for sleep disorder symptoms associated with sleep regulation. For example, the substantia nigra of brain 13 may play a role in regulating the sleep-wake cycle of patient 12; thus, delivery of electrical stimulation to the substantia nigra of brain 13 during a particular sleep stage may improve regulation of the sleep-wake cycle of patient 12.

In addition, patients with Parkinson's disease or other neurological disorders may have a poor quality of sleep associated with difficulty moving (e.g., akinesia, bradykinesia, or rigidity). Delivery of electrical stimulation to one or more regions of brain 13 may be an effective treatment for sleep disorder symptoms associated with or caused by the movement disorder. For example, electrical stimulation of the subthalamic nucleus of brain 13 during a particular sleep stage may increase the ability of patient 12 to initiate, maintain, or control movement naturally associated with or otherwise occurring during a particular sleep stage.

In addition, patients with movement disorders associated with a difficulty moving may find it difficult to get out of bed after waking up. Accordingly, upon determining that patient 12 is no longer in a sleep state (e.g., no longer asleep or attempting to sleep) based on biosignals within brain 13, DBS system 10 may control delivery of electrical stimulation to help patient 12 undergo the physical movements involved in getting out of bed or to otherwise initiate movement. In contrast, therapy systems that only rely on motion detectors (e.g., accelerometers) to control therapy delivery may be ineffective for patients with Parkinson's disease or other difficulty initiating movement, because the patient may be awake but unable to move. In other words, a therapy system that relies primarily on an accelerometer or other motion sensors may be unable to determine when a Parkinson's patient has woken up because the patient may be unable to move. In contrast, DBS system 10 may select a therapy program that helps improve the motor skills of patient 12 upon detecting the patient's awake state (i.e., detecting that patient 12 is not sleeping), such that patient 12 may initiate movement or maintain movement, e.g., to help patient 12 get out of bed.

IMD 16 includes a therapy module that includes a stimulation generator that generates and delivers electrical stimulation therapy to patient 12 via electrodes 22 of lead 20, as well as a processor that controls delivery of electrical stimulation based on a determined sleep stage of patient 12. In some examples, a processor of IMD 16 determines the sleep stage of patient 12 based on a frequency characteristic of one or more biosignals detected within brain 13 of patient 12 via electrodes 22 of lead 20, or via a separate electrode array that is electrically coupled to IMD 16 or to a separate sensing device. In addition, in some examples, the biosignal may be detected from external electrodes that are placed on the patient's scalp to sense brain signals instead of or in addition to implanted electrodes 22. Example techniques for determining a sleep state or sleep stage or patient 12 are described in U.S. Patent Application Publication No. 2009/0192556 by Wu et al., entitled "SLEEP STAGE DETECTION," which was filed on Sep. 25, 2008, and is herein incorporated by reference in its entirety.

Examples of biosignals indicative of activity within a brain of a patient include, but are not limited to, bioelectrical brain signals, such as electrical signals generated from local field potentials within one or more regions of brain 13, such as, but not limited to, an EEG signal or an ECoG signal. In some examples, the electrical signals within brain 13 may reflect changes in electrical current produced by the sum of electrical potential differences across brain tissue.

In some examples, the biosignals with which a sleep stage of patient 12 is determined are detected within the same tissue site of brain 13 as the target tissue site for delivery of electrical stimulation. In other examples, the biosignals may be detected within another tissue site. The target therapy delivery site may depend upon the patient disorder that is being treated with DBS system 10. In some examples, a biosignal may be detected within the thalamus, subthalamic nucleus, substantia nigra, internal globus pallidus, or pedunculopontine nucleus (PPN) of brain 13. In addition to or instead of detecting the biosignal within deep brain sites, the biosignal may be detected on a surface of brain 13, such as between the patient's cranium and the dura mater of brain 13.

In some examples, the target tissue site for the electrical stimulation delivered by IMD 16 may be selected based on biosignals detected within brain 13. For example, electrodes 22 can be positioned at specific target tissue sites within brain 13 by locating the target tissue sites based on certain characteristics of a sensed biosignal. For example, a particular structure or tissue site within brain 13 (e.g., the substantia nigra or subthalamic nucleus) may exhibit a biosignal signature (e.g., a signal characteristic such as a frequency band power level, ratio of power levels within two or more frequency bands, a peak, average or lowest biosignal amplitude within a particular range of time, a pattern in a biosignal amplitude over time, and the like), and the particular biosignal signature can be detected and used to identify the location within brain 13 for electrodes 22 before, during or after implantation. This may ensure that electrodes 22 are properly positioned within brain 13 to deliver efficacious stimulation therapy to patient 12, and that electrical stimulation configured for delivery to a particular structure or other tissue site within brain 13 is appropriately delivered to the target structure or other tissue site.

The biosignal signature that is associated with a particular portion of brain 13 and used to position electrodes 22 within the particular portion of brain 13 may be specific to patient 12 or may be a general signature applicable to more than one patient. A clinician may determine the biosignal signature for locating a target tissue site within brain 13 using any suitable technique. In some examples, biosignal sensing in conjunction with a medical imaging technique, such as functional magnetic resonance imaging (FMRI), can be used to locate a particular brain structure or other target tissue site and determine a biosignal signature that occurs within the brain structure or other target tissue site. Thereafter, upon determining the general location of the brain structure or other target tissue site (e.g., coarse tuning), a clinician may sense bioelectrical brain signals within brain 13 and locate the target brain structure or other target tissue site by determining the location at which a bioelectrical brain signal having the known biosignal signature is sensed (e.g., fine tuning the location for electrodes 22 based on a sensed biosignal).

In some examples, the clinician implants lead 20 in brain 13 and fine tunes the placement of electrodes 22 by sensing bioelectrical brain signals with electrodes 22 and locating the target brain structure or other target tissue site by determining the location at which the bioelectrical brain signal having the known biosignal signature is sensed. When electrodes 22 are appropriately positioned to deliver stimulation to the one or more target tissue sites within brain 13, DBS system 10 delivers therapy to patient 12 based on a determined sleep stage of patient 12. The biosignals that are analyzed to determine the position of electrodes 22 within brain 13 may be of the same type or of a different type than the biosignals used to determine the sleep stage of patient 12.

Electrical stimulation generated by IMD 16 may be configured to manage a variety of disorders and conditions. The therapy module within IMD 16 may generate the electrical stimulation signals using stimulation parameter values that are selected based on the determined patient sleep stage. In some examples, the stimulation generator of IMD 16 is configured to generate and deliver electrical pulses to patient 12. However, in other examples, the stimulation generator of IMD 16 may be configured to generate a continuous wave signal, e.g., a sine wave or triangle wave. The therapy module of IMD 16 may activate the generation and delivery of the electrical stimulation signal, deactivate generation and delivery of the electrical stimulation signal, increase an intensity (e.g. increase the amplitude, frequency, or pulse width) of a delivered electrical stimulation signal, or decrease an intensity (e.g. decrease the amplitude, frequency, or pulse width) of a delivered electrical stimulation signal based on a determined sleep stage.

IMD 16 may also generate the electrical stimulation therapy according to a therapy program that is selected at that given time in therapy. In examples in which IMD 16 delivers electrical stimulation in the form of stimulation pulses, a therapy program may include a set of therapy parameter values, such as an electrode combination for delivering stimulation to patient 12, pulse frequency, pulse width, and a current or voltage amplitude of the pulses. The electrode combination may indicate the specific electrodes 22 that are selected to deliver stimulation signals to brain 13 of patient 12, and also the respective polarity of the selected electrodes. IMD 16 may also deliver continuous waveform stimulation signals (e.g., stimulation signals having a sine waveform).

While the description of DBS system 10 is primarily directed to examples in which IMD 16 (e.g., a processor of IMD 16) determines a sleep stage of patient 12 and controls delivery of electrical stimulation based on the determined sleep stage, in other examples, a device separate from IMD 16, such as programmer 14, a sensing module that is separate from IMD 16, or another computing device, may determine the sleep stage of patient 12 and provide the indication to IMD 16. Furthermore, although IMD 16 may control delivery of electrical stimulation based on the determined sleep stage, in other examples, another device (e.g., programmer 14) may control delivery of electrical stimulation based on the determined patient sleep stage, whether the patient sleep stage is determined by IMD 16 or a separate device, and input the electrical stimulation parameter values of the therapy program to IMD 16. Moreover, in some examples, IMD 16 or another device may select a therapy program group based on a detected sleep stage, where the therapy program group includes two or more therapy programs. The stimulation therapy according to the therapy programs of the group may be delivered simultaneously or alternatively, either in an overlapping or non-overlapping manner.

IMD 16 may be implanted within a subcutaneous pocket above the clavicle, or, alternatively, the abdomen, back or buttocks of patient 12. Implanted lead extension 18 is coupled to IMD 16 via connector 24 (also referred to as a header of IMD 16). In the example of FIG. 1, lead extension 18 traverses from the implant site of IMD 16 and along the neck of patient 12 to cranium 26 of patient 12 to access brain 13. In the example shown in FIG. 1, lead 20 is implanted within brain 13 of patient 12 in order to deliver electrical stimulation to one or more regions of brain 13, which may be selected based on the patient condition or disorder controlled by DBS system 10. Other lead 20 and IMD 16 implant sites and configurations are contemplated. For example, IMD 16 may be implanted on or within cranium 26. Furthermore, DBS system 10 may comprise more than one lead and more than one set of electrodes. External programmer 14 wirelessly communicates with IMD 16 as needed to provide or retrieve therapy information.

Lead 20 may be positioned to deliver electrical stimulation to one or more target tissue sites within brain 13 to manage patient symptoms associated with the sleep impairment of patient 12, which, in some cases, is associated with a neurological disorder of patient 12, such as a movement disorder. In the example shown in FIG. 1, lead 20 is positioned to provide electrical stimulation to patient 12 to manage sleep impairment associated with sleep regulation and movement during a sleep stage, as well as to provide electrical stimulation to patient 12 to manage a movement disorder. For example, lead 20 can be implanted within brain 13 in order to deliver electrical stimulation to the substantia nigra via set of electrodes 22B and the subthalamic nucleus via set of electrodes 22A of the single lead 20, where the sets of electrodes 22A and 22B are positioned to independently stimulate the substantia nigra and the subthalamic nucleus. That is, IMD 16 can independently select the set of electrodes 22A (and not electrodes 22B) to deliver stimulation to the subthalamic nucleus or independently select the set of electrodes 22B (and not electrodes 22A) to deliver stimulation to the substantia nigra.

Stimulation to the substantia nigra and subthalamic nucleus can have different physiological effects on patient 12. Thus, the independently selectable electrodes 22A, 22B that are positioned to deliver stimulation to respective target tissue sites provides IMD 16 with a plurality of configurations with which stimulation therapy can be delivered to patient 12. In some examples, sets of electrodes 22A, 22B share at least one electrode, while in other examples, sets of electrodes 22A, 22B do not have any common electrodes and are comprised of separate sets of electrodes.

Lead 20 may be implanted to position electrodes 22 at desired locations of brain 13 through a hole in cranium 26. Lead 20 may be placed at any location within brain 13 such that electrodes 22 are capable of providing electrical stimulation to target tissue sites within brain 13 during treatment. For example, in examples, electrodes 22 may be surgically implanted under the dura mater of brain 13 or within the cerebral cortex of brain 13 via a burr hole in cranium 26 of patient 12, and electrically coupled to IMD 16 via one or more leads 20.

Example techniques for delivering therapy to manage a movement disorder are described in U.S. Patent Application Publication No. 2009/0099627 by Molnar et al., entitled "THERAPY CONTROL BASED ON A PATIENT MOVEMENT STATE," which was filed on Sep. 25, 2008, U.S. Provisional Patent Application No. 60/999,096 by Molnar et al., entitled "DEVICE CONTROL BASED ON PROSPECTIVE MOVEMENT," which was filed on Oct. 16, 2007, and U.S. Provisional Patent Application No. 60/999,097 by Denison et al., entitled "RESPONSIVE THERAPY SYSTEM," which was filed on Oct. 16, 2007. The entire contents of the above-identified U.S. Patent Application Publication No. 2009/0099627 and U.S. Provisional Patent Application Nos. 60/999,096 and 60/999,097 are incorporated herein by reference. In some examples described by U.S. Patent Application Publication No. 2009/0099627 and U.S. Provisional Patent Application No. 60/999,096, brain signals are detected within a dorsal-lateral prefrontal (DLPF) cortex of a patient and are indicative of prospective movement of the patient. The signals within the DLPF cortex that are indicative of prospective patient movement may be used to control the delivery of movement disorder therapy, such as delivery of electrical stimulation, fluid delivery or a sensory cue (e.g., visual, somatosensory, or auditory cue).

In some examples described by U.S. Patent Application Publication No. 2009/0099627 and U.S. Provisional Patent Application Ser. No. 60/999,097, a brain signal, such as an EEG or ECoG signal, may be used to determine whether a patient is in a movement state or a rest state. The movement state includes the state in which the patient is generating thoughts of movement (i.e., is intending to move), attempting to initiate movement, or is moving. The rest state, in which patient is not generating thoughts of movement (i.e., is intending to move), attempting to initiate movement, or is moving, can be used to detect a sleep state of patient 12 in some examples. The movement state or rest state determination may then be used to control therapy delivery. For example, upon detecting a movement state of the patient, IMD 16 can deliver stimulation therapy to the subthalamic nucleus of brain 13 of patient 12 in order to help manage movement disorder symptoms of patient 12. IMD 12 can deliver therapy to brain 13 (e.g., the subthalamic nucleus) in order to help the patient initiate movement or maintain movement, and, upon detecting a rest state of the patient, therapy delivery may be deactivated or otherwise modified.

In the example shown in FIG. 1, electrodes 22 of lead 20 are shown as ring electrodes. Ring electrodes may be used in DBS applications because they are relatively simple to program and are capable of delivering an electrical field to any tissue adjacent to electrodes 22. In other examples, electrodes 22 may have different configurations. For example, in some examples, electrodes 22 of lead 20 may have a complex electrode array geometry that is capable of producing shaped electrical fields. The complex electrode array geometry may include multiple electrodes (e.g., partial ring or segmented electrodes) around the outer perimeter of lead 20, rather than one ring electrode. In this manner, electrical stimulation may be directed to a specific direction from lead 20 to enhance therapy efficacy and reduce possible adverse side effects from stimulating a large volume of tissue. In some examples, a housing of IMD 16 may include one or more stimulation and/or sensing electrodes. In alternative examples, lead 20 may have a shape other than an elongated cylinder as shown in FIG. 1. For example, lead 20 may be a paddle lead, a spherical lead, a bendable lead, or any other type of shape effective in treating patient 12.

In the example shown in FIG. 1, IMD 16 includes a memory to store a plurality of therapy programs that each defines a set of electrical stimulation parameter values. Upon determining a current sleep stage of patient 12, e.g., by monitoring biosignals within brain 13, IMD 16 may select a therapy program from the memory, where the therapy program is associated with the current sleep stage, and generate the electrical stimulation to manage the patient symptoms associated with the determined sleep stage using the selected therapy program. If DBS system 10 is configured to provide therapy during a plurality of patient sleep stages, each sleep stage may be associated with a different therapy program because different therapy programs may provide more effective therapy for a certain sleep stage compared to other therapy programs. Alternatively, two or more sleep stages may be associated with a common therapy program. Accordingly, IMD 16 may store a plurality of therapy programs or programmer 14 may store a plurality of therapy programs that are provided to IMD 16 via wireless telemetry.

During a trial stage in which IMD 16 is evaluated to determine whether IMD 16 provides efficacious therapy to patient 12, a plurality of therapy programs may be tested and evaluated for efficacy relative to one or more sleep stages. For example, a clinician may observe patient 12 during the sleep state and modify therapy delivery to patient 12 during each of the plurality of sleep stages in order to determine which therapy programs (e.g., sets of therapy parameter values) provide efficacious therapy to patient 12 during the respective sleep stage. In some examples, patient 12 can provide feedback (when in the awake state) as to the quality of the sleep state, which can indicate whether the trial therapy programs selected for delivery during the sleep stages were efficacious. While a clinician can (but need not) rely on a known set of parameter values to initiate the trial therapy delivery, different therapy parameter values may provide efficacious therapy for different patients. Therapy programs may be selected for storage within IMD 16 based on the results of the trial stage. Therefore, the trial stage may be useful for customizing the therapy parameter values stored and implemented by IMD 16 for a particular patient 12.

During chronic therapy in which IMD 16 is implanted within patient 12 for delivery of electrical stimulation on a non-temporary basis, different therapy programs may be delivered to patient 12 based on a determined sleep stage of patient 12. As previously described, in some examples, IMD 16 may automatically determine the current sleep stage of patient 12 based on one or more biosignals, or may receive input from another device that automatically determines the sleep stage of patient 12. In addition, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust electrical stimulation parameters, switch between programs, or undertake other therapy adjustments. Patient 12 may generate additional programs for use by IMD 16 via external programmer 14 at any time during therapy delivery or as designated by the clinician.

Generally, IMD 16 is constructed of a biocompatible material that resists corrosion and degradation from bodily fluids. IMD 16 may comprise a hermetic housing or a near hermetic housing to substantially enclose components, such as a processor, therapy module, and memory. IMD 16 may be implanted within a subcutaneous pocket close to the stimulation site. As previously described, although IMD 16 is implanted within a subcutaneous pocket above the clavicle of patient 12 in the example shown in FIG. 1, in other examples, IMD 16 may be implanted on or within cranium 26, within the patient's back, abdomen, or any other suitable place within patient 12.

Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify electrical stimulation parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of lead 20 and the electrode 22 arrangement, the position of lead 20 within brain 13, the configuration of electrode array 22, initial programs defining electrical stimulation parameter values, and any other information the clinician desires to program into IMD 16. Programmer 14 may also be capable of completing functional tests (e.g., measuring the impedance of electrodes 22).

Programmer 14 may be used by a clinician to control delivery of electrical stimulation, such as by activating electrical stimulation, deactivating electrical stimulation, increasing an intensity of electrical stimulation, or decreasing an intensity of electrical stimulation based on a sleep stage of patient 12. The clinician may also store therapy programs within IMD 16 with the aid of programmer 14. During a programming session, the clinician may determine one or more therapy programs that may provide efficacious therapy to patient 12 to address symptoms associated with one or more different patient sleep stages. Patient 12 may provide feedback to the clinician as to the efficacy of the specific program being evaluated. Once the clinician has identified one or more therapy programs that may be efficacious in managing one or more sleep stages of patient 12, patient 12 may continue the evaluation process and identify, for each of the patient sleep stages, the one or more programs that best mitigate symptoms associated with the sleep stage. The evaluation of therapy programs may be completed after patient 12 wakes up. In some cases, the same therapy program may be applicable to two or more sleep stages. Programmer 14 may assist the clinician in the creation/identification of therapy programs by providing a methodical system for identifying potentially beneficial electrical stimulation parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain electrical stimulation parameters or set an available range of values for a particular electrical stimulation parameter.

Programmer 14 may also provide an indication to patient 12 when therapy is being delivered, when patient input has triggered a change in electrical stimulation parameters or when the power source within programmer 14 or IMD 16 needs to be replaced or recharged. For example, programmer 14 may include an alert LED, may flash a message to patient 12 via a programmer display, or may generate an audible sound or somatosensory cue to confirm patient input was received, e.g., to indicate a patient state or to manually modify an electrical stimulation parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth™ specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

DBS system 10 may be implemented to provide chronic stimulation therapy to patient 12 over the course of several months or years. However, DBS system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
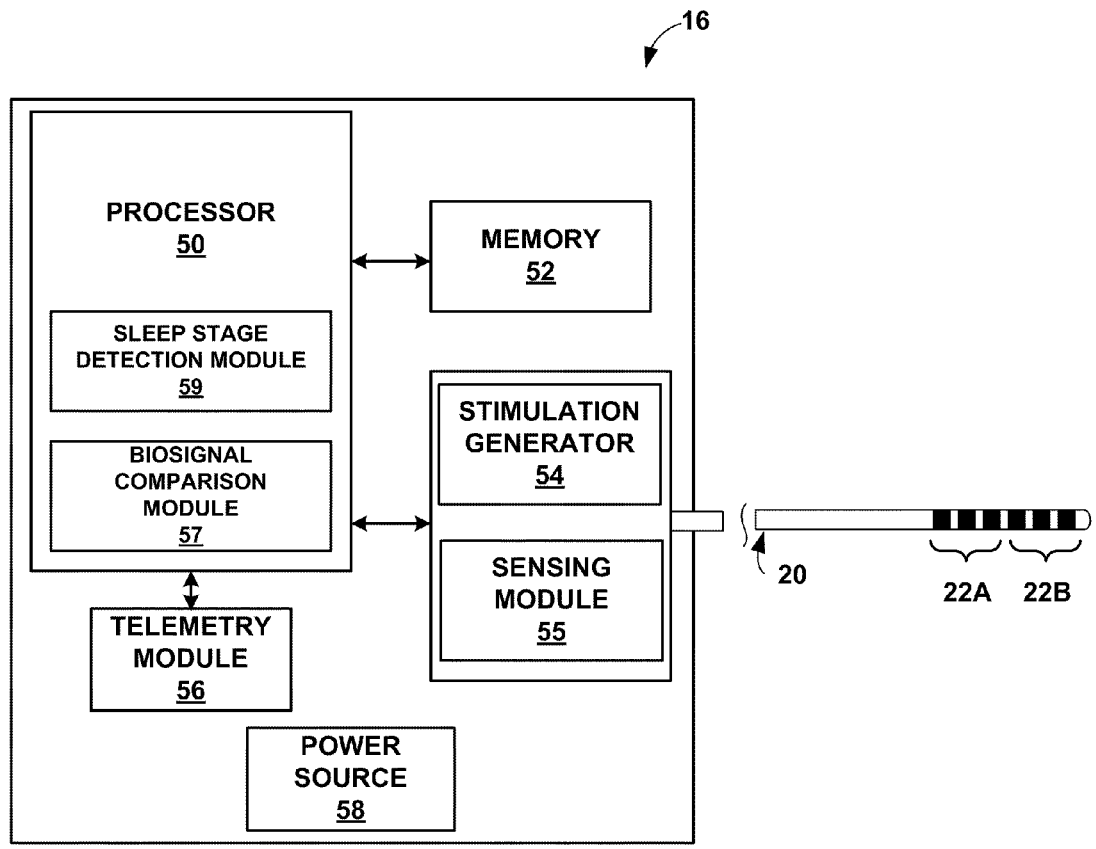
FIG. 2 is a functional block diagram illustrating components of an example medical device.

FIG. 2 is a functional block diagram illustrating components of an example IMD 16. In the example shown in FIG. 2, IMD 16 generates and delivers electrical stimulation therapy to patient 12. IMD 16 includes processor 50, memory 52, stimulation generator 54, sensing module 55, telemetry module 56, biosignal comparison module 57, power source 58, and sleep stage detection module 59. Although biosignal comparison module 57 and sleep stage detection module 59 are shown to be components of processor 50 in FIG. 2, in other examples, biosignal comparison module 57, sleep stage detection module 59, and processor 50 may be separate components and may be electrically coupled, e.g., via a wired or wireless connection.

Memory 52 may include any volatile or non-volatile media, such as a random access memory (RAM), read only memory (ROM), non-volatile RAM (NVRAM), electrically erasable programmable ROM (EEPROM), flash memory, and the like. Memory 52 may store instructions for execution by processor 50 and information defining delivery of electrical stimulation to patient 12, such as, but not limited to, therapy programs (e.g., sets of stimulation parameter values) or therapy program groups, information associating therapy programs with one or more sleep stages, thresholds or other information used to detect a sleep state, movement state, and specific sleep stages based on biosignals, information regarding biosignals of target tissue sites of patient 12, and any other information regarding therapy of patient 12. Therapy information may be recorded in memory 52 for long-term storage and retrieval by a user. As described in further detail with reference to FIG. 3, memory 52 may include separate memories for storing information, such as separate memories for therapy programs, sleep stage information, diagnostic information, target tissue site information, and patient information. In some examples, memory 52 stores program instructions that, when executed by processor 50, cause IMD 16 and processor 50 to perform the functions attributed to them herein.

Processor 50 controls stimulation generator 54 to deliver electrical stimulation therapy via lead 20. An example range of electrical stimulation parameters believed to be effective in DBS delivered to a substantia nigra of brain 13 (FIG. 1) to manage symptoms present during a sleep state include:

1. Frequency: between approximately 0.1 Hz and approximately 500 Hz, such as between approximately 0.5 Hz and 200 Hz. In some cases, the frequency of stimulation may change during delivery of stimulation, and may be modified, for example, based on the sensed sleep stage or a pattern of sensed biosignals during the sleep state. For example, the frequency of stimulation may have a pattern within a given range, such as a random or pseudo-random pattern within a frequency range of approximately 5 Hz to approximately 150 Hz around a central frequency. In some examples, the waveform may also be shaped based on a sensed signal to either be constructive or destructive in a complete or partial manner, or phased shifted from about 0 degrees to about 180 degrees out of phase.

2. Amplitude: between approximately 0.1 volts and approximately 50 volts. In other examples, rather than a voltage controlled system, the stimulation system may control the current.

3. Pulse Width: between approximately 10 microseconds and approximately 5000 microseconds, such as between approximately 100 microseconds and approximately 1000 microseconds, or between approximately 180 microseconds and approximately 450 microseconds.

The electrical stimulation parameter values provided above, however, may differ from the given ranges depending upon the particular patient and the particular sleep stage (e.g., Stage 1, Stage 2, Deep Sleep, or REM) of the sleep state. For example, with respect to the sleep stage, the electrical stimulation parameter values may be modified based on the sleep stage during which electrical stimulation is provided (e.g., Stage 1, Stage 2, Deep Sleep or REM). As described in further detail below, in some examples, it may be desirable for stimulation generator 54 to deliver stimulation to patient 12 during some sleep stages, and deliver minimal or no stimulation during other sleep stages.

An example range of electrical stimulation parameters defining stimulation therapy delivered to a subthalamic nucleus of brain 13 that are believed to be effective in DBS to manage a movement disorder of patient 12 include:

1. Frequency: between approximately 100 Hz and approximately 500 Hz, such as approximately 130 Hz.

2. Voltage Amplitude: between approximately 0.1 volts and approximately 50 volts, such as between approximately 0.5 volts and approximately 20 volts, or approximately 5 volts. In other examples, rather than a voltage controlled system, the stimulation system may control the current.

3. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Other ranges of therapy parameter values may also be useful, and may depend on the target stimulation site within patient 12. While stimulation pulses are described, stimulation signals may be of any form, such as continuous-time signals (e.g., sine waves) or the like.

As described in further detail below, processor 50 can control stimulation generator 54 to generate stimulation that is delivered to the substantia nigra of brain 13 of patient 12 and the subthalamic nucleus of brain 13 according to the stimulation parameters of different therapy programs. In each of the examples described herein, if stimulation generator 54 shifts the delivery of stimulation energy between two therapy programs, processor 50 of IMD 16 may provide instructions that cause stimulation generator 54 to time-interleave stimulation energy between the electrode combinations of the two therapy programs, as described in U.S. Pat. No. 7,519,431 issued to Steven Goetz et al. on Apr. 14, 2009, entitled "SHIFTING BETWEEN ELECTRODE COMBINATIONS IN ELECTRICAL STIMULATION DEVICE," the entire content of which is incorporated herein by reference.

In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs may be used in other examples.

Processor 50 may also control delivery of electrical stimulation to patient 12 by delivering electrical stimulation to one target tissue site with particular electrodes (e.g., electrodes 22A of DBS system 10) and to another target tissue site with different electrodes (e.g., electrodes 22B of DBS system 10). For example, as discussed in more detail with reference to FIG. 5, electrical stimulation may be delivered to the subthalamic nucleus of brain 13 of patient 12 via electrodes 22A and to the substantia nigra of brain 13 of patient 12 via electrodes 22B. In some cases, electrical stimulation may be delivered via electrodes 22A according to a particular therapy program and via electrodes 22B according to a different therapy program (e.g., defining at least one different stimulation parameter value than the therapy program delivered via electrodes 22A to the subthalamic nucleus). Electrical stimulation via electrodes 22A and 22B may be controlled independently, and may be controlled and delivered either simultaneously or alternatively. In other examples, processor 50 may control delivery of electrical stimulation by delivering electrical stimulation to several different target tissue sites with some or all of the same electrodes.

Processor 50 may include any one or more of a microprocessor, a controller, a digital signal processor (DSP), an application specific integrated circuit (ASIC), a field-programmable gate array (FPGA), discrete logic circuitry, and the functions attributed to processor 50 herein may be embodied as firmware, hardware, software or any combination thereof. In general, components described as processors within IMD 12, external programmer 14 or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and embodied as software, firmware, hardware, or any combination thereof.

Sleep stage detection module 59 determines a current sleep stage of patient 12 based on a sensed biosignal. As described in further detail below, in some examples, sleep stage detection module 59 may be coupled to sensing module 55, which generates a signal indicative of electrical activity within brain 13 of patient 12, as shown in FIG. 2. In this way, sensing module 55 may detect or sense a biosignal within brain 13 of patient 12. Although sensing module 55 is incorporated into a common housing with stimulation generator 54 and processor 50 in FIG. 2, in other examples, sensing module 55 may be in a separate housing from IMD 16 and may communicate with processor 50 via wired or wireless communication techniques.

Sensing module 55 is configured to generate an electrical signal indicative of activity within brain 13 of patient and/or other physiological parameters of patient 12. As previously indicated, example electrical signals that sensing module 55 may sense include, but are not limited to, a signal generated from local field potentials within one or more regions of brain 13. EEG and ECoG signals are examples of local field potentials that may be measured within brain 13. However, local field potentials may include a broader genus of electrical signals within brain 13 of patient 12.

In some examples, such as during initial implant of lead 20 or during a periodic electrode location check, sensing module 55 can sense a biosignal within brain 13 and processor 50 may determine the position of electrodes 22 within brain 13 based on the sensed biosignal. Processor 50 may periodically (e.g., daily, once a week, or more or less frequently) determine whether electrodes 22 are properly positioned to deliver stimulation to the one or more target tissue sites within brain 13 (e.g., the substantia nigra or subthalamic nucleus). For example, as mentioned previously, a particular structure or tissue site within brain 13 (e.g. the substantia nigra) may exhibit a biosignal signature (e.g., a particular signal characteristic) that may be detected and used to indicate the location of a particular electrode 22 within brain 13.

Sensing module 55 may detect or sense a biosignal within brain 13 of patient 12 and transmit the sensed information to biosignal comparison module 57. In some examples, biosignal comparison module 57 accesses memory 52 to retrieve one or more previously recorded biosignals of one or more target tissue sites that are stored in memory 52. Biosignal comparison module 57 may compare the detected biosignal to the previously recorded biosignal of the target tissue site in order to determine whether electrodes 22 are properly positioned at the target tissue site. For example, biosignal comparison module 57 may compare a particular characteristic of the detected biosignal to the same characteristic (e.g., a signature biosignal characteristic) of the previously recorded biosignal to determine whether the characteristics are the same. Example signal characteristics that can be compared include, but are not limited to, a power level within one or more frequency bands, a ratio of power levels within two or more frequency bands, a peak, average or lowest biosignal amplitude within a particular range of time, a pattern in a biosignal amplitude over time, and the like.

If the signal characteristics between the sensed biosignal and the stored biosignal substantially match (e.g., are within a threshold range, which may be, for example about 75% to about 100%), biosignal comparison module 57 may determine that electrodes 22 used to detect the biosignal are implanted within the target tissue site (e.g., subthalamic nucleus and/or substantia nigra) associated with the biosignal characteristic. If biosignal comparison module 57 determines that the detected biosignal does not substantially match the previously recorded biosignal characteristic, processor 50 may send an indication (e.g., a wireless signal) to programmer 14 or another external device to notify a clinician, patient caretaker, or machine that lead 20 may have migrated, such that electrodes 22 are no longer positioned to deliver electrical stimulation to at least one of the subthalamic nucleus, substantia nigra, or another target tissue site. Additionally or alternatively, processor 50 may modify stimulation parameters being delivered by stimulation generator 54 if the detected biosignal does not match the predetermined biosignal characteristic.

In addition to or instead of comparing the characteristic of the biosignal to a stored signal, biosignal comparison module 57 compares a characteristic of a biosignal sensed via a specific subset of electrodes 22 to a template or threshold stored by memory 52 in order to determine whether the subset of electrodes 22 are positioned at the target tissue site. The template or threshold stored by memory 52 can be associated with the target tissue site. For example, the template or threshold can be the biosignal signature that is associated with the target tissue site, as discussed above.

Figure 6:
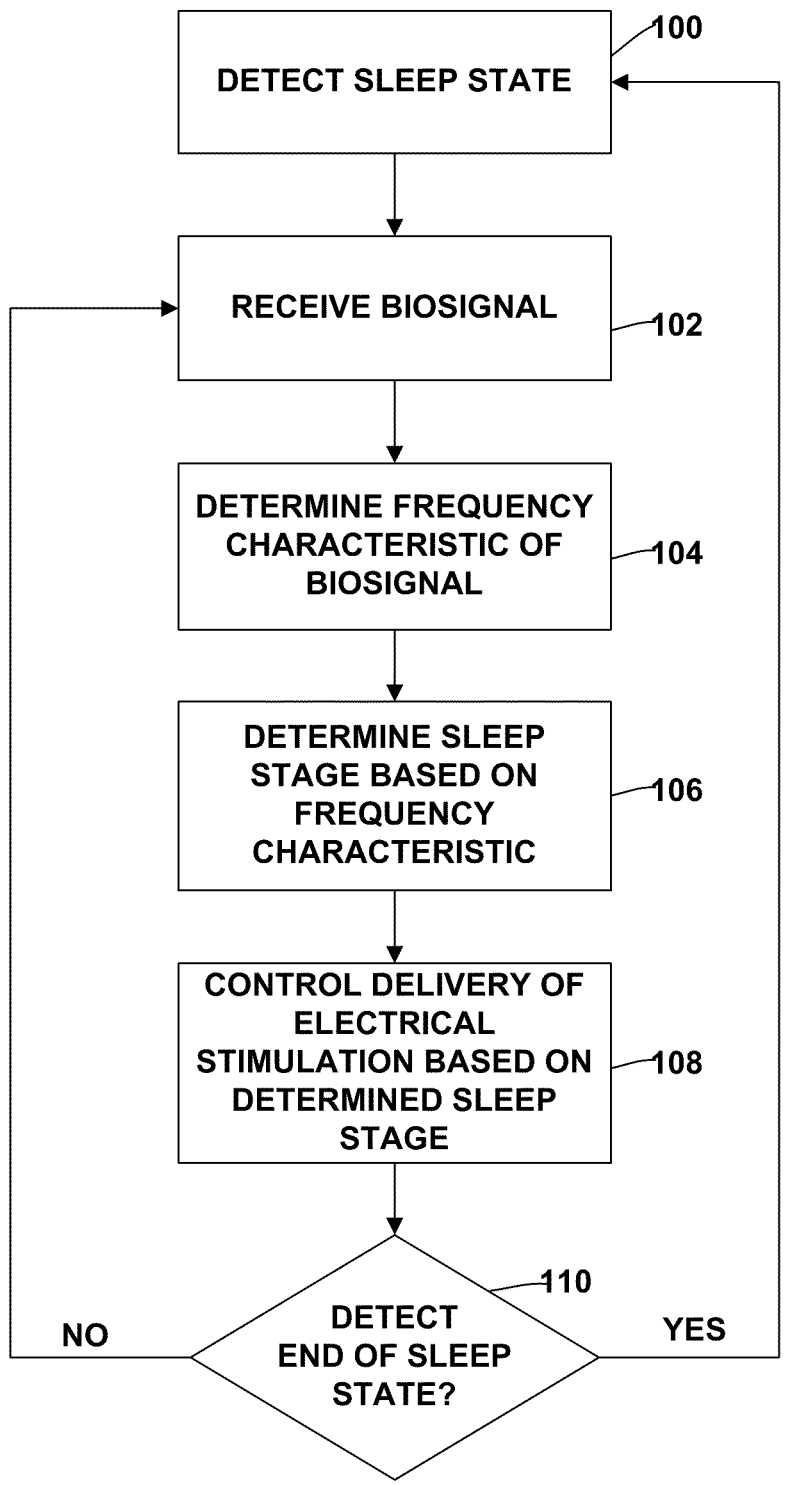
FIG. 6 is a flow diagram illustrating an example technique for controlling therapy delivery to a brain of a patient based on a determined patient sleep stage.

As described in further detail with respect to FIG. 6, processor 50 can determine a current sleep stage of patient 12 based on a biosignal sensed by sensing module 55. In some examples, sensing module 55 generates a signal indicative of brain activity of patient 12 (e.g., by determining tissue potentials across electrodes 22), and sleep stage detection module 59 analyzes the signal to determine a current sleep stage of patient 12. In addition to or instead of monitoring biosignals of patient 12 via electrodes 22 coupled to lead 20, sleep stage detection module 59 may directly or indirectly receive biosignals indicative of electrical activity within brain 13 from electrodes coupled to another lead that is electrically coupled to sensing module 55, biosignals from electrodes coupled to an outer housing of IMD 16 and electrically coupled to sensing module 55, and/or biosignals from a sensing module that is separate from IMD 16.

Upon determining the patient's current sleep stage, sleep stage detection module 59 may generate a sleep stage indication. The sleep stage indication may be a value, flag, or signal that is stored or transmitted to indicate the current sleep stage of patient 12. In some examples, sleep stage detection module 59 may transmit the sleep stage indication to another device, such as programmer 14, via telemetry module 56.

Processor 50 may control delivery of electrical stimulation to the substantia nigra and the subthalamic nucleus of brain 13 of patient 12 based on the sleep stage indication. In some examples, processor 50 may control delivery of electrical stimulation as shown in Table 1.

TABLE 1

Delivery of DBS based on determined sleep stage.

| | Substantia Nigra (SN) | Subthalamic Nucleus (STN) |
|---|---|---|
| Stage 1 | Deliver stimulation | Deliver stimulation |
| REM | Deliver stimulation | Deliver stimulation |
| Stage 2 | Deliver stimulation | Deliver minimal to no stimulation |
| Deep Sleep | Deliver minimal to no stimulation | Deliver minimal to no stimulation |

For example, as previously mentioned, during the Stage 1 sleep stage, patient 12 may be in the beginning stages of sleep and may begin to lose conscious awareness of the external environment. During the REM sleep stage, patient 12 may exhibit increased heart rate and respiration. In these sleep stages, patient 12 may require electrical stimulation configured to assist patient 12 in initiating sleep or maintaining a sleep stage with relatively more brain activity than the Stage 2 or Deep Sleep sleep stages. Because the substantia nigra may play a role in sleep regulation, processor 50 may adjust and deliver electrical stimulation to the substantia nigra of brain 13 of patient 12 during the Stage 1 and REM sleep stages. In some examples, stimulation generator 54 does not generate and deliver electrical stimulation to the substantia nigra of brain 13 of patient 12 during the other sleep stages, such as during the Deep Sleep sleep stage. However, in some examples, stimulation generator 54 delivers a lower intensity of electrical stimulation (e.g., as indicated by a lower amplitude or frequency, or a shorter pulse width) to the substantia nigra during the Stage 2 and/or Deep Sleep sleep stages, relative to the intensity of electrical stimulation delivered during the Stage 1 and REM sleep stages or relative to a respective threshold value.

Patient 12 may undergo relatively more motor activity during the Stage 1 and REM sleep stages than during the Stage 2 and Deep Sleep sleep stages. Accordingly, processor 50 may adjust and deliver electrical stimulation to the subthalamic nucleus of patient 12 during the Stage 1 and REM sleep stages to help improve the motor function of patient 12, which may improve patient sleep quality. In some examples, stimulation generator 54 does not generate and deliver electrical stimulation to the subthalamic nucleus of brain 13 of patient 12 during the other sleep stages, such as during the Stage 2 and/or Deep Sleep sleep stages. However, in some examples, stimulation generator 54 delivers a lower intensity of electrical stimulation (e.g., as indicated by a lower amplitude, frequency or shorter pulse width) to the subthalamic nucleus during the Stage 2 and/or Deep Sleep sleep stages relative to the intensity of electrical stimulation delivered during the Stage 1 and REM sleep stages or relative to a respective threshold value.

Therefore, if sleep stage detection module 59 determines that patient 12 is in either the Stage 1 or REM sleep stages, processor 50 may control stimulation generator 54 to activate or increase an intensity of electrical stimulation delivered to the substantia nigra and subthalamic nucleus based on the sleep stage indication generated by sleep stage detection module 59. The intensity of electrical stimulation delivered to the substantia nigra may be increased relative to a previously set value (e.g., a stimulation parameter value for a previously determined sleep stage) or relative to a baseline intensity level (e.g., as indicated by a particular stimulation threshold). In some examples, memory 52 of IMD 16 stores the baseline intensity level, which can be a minimum stimulation intensity level that is delivered to brain 13 of patient 12 regardless of a detected sleep state in order to maintain a particular patient state, such as a baseline state in which the patient symptoms are manageable. Despite the patient symptoms being manageable, further therapy delivery can be desirable in order to improve the patient state relative to the baseline state.

Additionally or alternatively, processor 50 may also decrease an intensity of the electrical stimulation delivered to the substantia nigra and the subthalamic nucleus if patient 12 is in either the Stage 1 or REM sleep stages, depending upon the previous electrical stimulation settings. For example, if patient 12 has just entered the Stage 1 sleep stage for the first time during a sleep state, processor 50 may not necessarily decrease an intensity of electrical stimulation delivered to the substantia nigra or the subthalamic nucleus because no previous delivery of electrical stimulation may have occurred. However, because patient 12 may cycle through the sleep stages, patient 12 may be in a sleep stage other than Stage 1 prior to re-entering the Stage 1 sleep stage. Thus, in some cases, processor 50 may decrease an intensity of electrical stimulation delivered to the substantia nigra and subthalamic nucleus of patient 12 in response to determining that patient 12 is in the Stage 1 sleep stage, e.g., if the therapy delivered during the previously detected sleep state had a higher intensity than that desired for the Stage 1 sleep stage.

Processor 50 may activate, increase an intensity, or decrease an intensity of electrical stimulation by selecting therapy programs and/or modifying electrical stimulation parameters of one or more currently selected therapy programs, or may deliver electrical stimulation according to one or more therapy programs selected from memory 52 based on a determination that patient 12 is in one of the Stage 1 or REM sleep stages. In some examples, in order to maintain a minimum level of stimulation intensity during the Stage 1 and/or REM sleep stages, processor 50 controls stimulation generator 54 to deliver stimulation therapy having a stimulation parameter value (e.g., a voltage or current amplitude, a frequency or a pulse width) greater than a threshold value to the substantia nigra of brain 13 during the Stage 1 and/or REM sleep stages. In addition, processor 50 can control stimulation generator 54 to deliver stimulation therapy having a stimulation parameter value (e.g., a voltage or current amplitude, a frequency or a pulse width) greater than a threshold value to the subthalamic nucleus of brain 13 during the Stage 1 and/or REM sleep stages. The threshold values used to determine the minimum intensity of therapy delivered to the substantia nigra and the subthalamic nucleus can be different or the same.

In some examples, processor 50 may selectively control delivery of electrical stimulation by stimulation generator 54 to the substantia nigra and subthalamic nucleus of brain 13 during the Stage 2 and Deep Sleep sleep stages. During the Stage 2 and Deep Sleep stages, muscular activity of patient 12 may decrease and conscious awareness of the external environment may disappear. During the Stage 2 sleep stage, patient 12 may continue to require adjustment and delivery of electrical stimulation to the substantia nigra in order to maintain the sleep stage. Thus, processor 50 may activate, increase an intensity of electrical stimulation, or decrease an intensity of electrical stimulation delivered to the substantia nigra in order to maintain the Stage 2 sleep stage, depending upon the previous sleep stage of patient 12 and depending upon the previous electrical stimulation settings. However, processor 50 controls stimulation generator 54 to deliver stimulation therapy to the substantia nigra of brain 13 during the Stage 2 sleep stage. In some examples, the processor 50 controls stimulation generator 54 to deliver stimulation therapy having a stimulation parameter value (e.g., a voltage or current amplitude, a frequency or a pulse width) greater than a threshold value to the substantia nigra of brain 13 during the Stage 2 sleep stage.

During the Stage 2 sleep stage, patient 12 may also exhibit relatively less motor activity than during the Stage 1 or REM sleep stages but relatively more motor activity than during the Deep Sleep sleep stage. Consequently, in some cases, patient 12 may continue to require delivery and adjustment of electrical stimulation to the subthalamic nucleus during the Stage 2 sleep stage in order to control the symptoms of the sleep disorder associated with movement. Therefore, in some cases, as shown in Table 1 above, processor 50 controls stimulation generator 54 to deliver stimulation therapy to the subthalamic nucleus of brain 13 during the Stage 2 sleep stage. For example, processor 50 may activate, increase or decrease an intensity of electrical stimulation delivered to the subthalamic nucleus during the Stage 2 sleep stage. In some examples, processor 50 controls stimulation generator 54 to deliver stimulation therapy having a stimulation parameter value (e.g., a voltage or current amplitude, a frequency or a pulse width) greater than a threshold value to the subthalamic nucleus of brain 13 during the Stage 2 sleep stage. The threshold value may be different from that used to control the stimulation therapy to the substantia nigra during the Stage 2 sleep stage.

However, in some cases, the Stage 2 sleep stage of patient 12 may naturally require almost no movement and patient 12 may not consciously move as much as in other sleep stages. For example, patient 12 may not experience involuntary movements or at least experience minimal involuntary movements. Thus, patient 12 may not require stimulation of the subthalamic nucleus during the Stage 2 sleep stage. Thus, processor 50 may activate, deactivate or decrease an intensity of electrical stimulation delivered to the subthalamic nucleus during the Stage 2 sleep stage based on the sleep stage indication generated by sleep stage detection module 59. In some examples, the processor 50 controls stimulation generator 54 to deliver stimulation therapy having a stimulation parameter value (e.g., a voltage or current amplitude, a frequency or a pulse width) less than a threshold value to the subthalamic nucleus of brain 13 during the Stage 2 sleep stage. In some examples, the stimulation delivered to the subthalamic nucleus during the Stage 2 sleep stage has a lower intensity than that delivered to the subthalamic nucleus during the Stage 1 and REM sleep stages.

During the Deep Sleep sleep stage, patient 12 may require little to no delivery of electrical stimulation to the substantia nigra and the subthalamic nucleus compared to the parameters delivered during the Stage 1, Stage 2, or REM sleep stages. If patient 12 is in the Deep Sleep sleep stage, processor 50 may deactivate or decrease the intensity of electrical stimulation delivered to the substantia nigra and the subthalamic nucleus relative to the intensity of electrical stimulation delivered during the Stage 1, Stage 2, or REM sleep stages based on the Deep Sleep sleep stage indication generated by sleep stage detection module 59. In some examples, processor 50 controls stimulation generator 54 to deliver stimulation therapy having a stimulation parameter value (e.g., a voltage or current amplitude, a frequency or a pulse width) lower than a first threshold values to the substantia nigra of brain 13 during the Deep Sleep sleep stage. The threshold value may be different from that used to control the stimulation therapy to the substantia nigra during the Stage 2 sleep stage and may be lower than that used to control stimulation therapy to the substantia nigra during the Stage 1 and REM sleep stages.

In addition, in some examples, processor 50 controls stimulation generator 54 to deliver stimulation therapy having a stimulation parameter value (e.g., a voltage or current amplitude, a frequency or a pulse width) lower than a second threshold value to the subthalamic nucleus of brain 13 during the Deep Sleep sleep stage. The threshold value may be different from that used to control the stimulation therapy to the subthalamic nucleus during the Stage 2 sleep stage and may be lower than that used to control stimulation therapy to the subthalamic nucleus during the Stage 1 and REM sleep stages.

In the example shown in FIG. 2, processor 50 may select one or more therapy programs from memory 52 or modify one or more of the stimulation parameter values of one or more stored therapy programs based on the sleep stage indication generated by sleep stage detection module 59 and control the delivery of electrical stimulation accordingly. Alternatively, processor 50 may select one or more therapy programs from memory 52 (e.g., by selecting a stored therapy program or selecting instructions reflecting modifications to a stored therapy program) and transmit the selected therapy program(s) to processor 50, which may then control stimulation generator 54 to deliver therapy according to the selected therapy program(s).

The "selected" therapy program(s) may include, for example, a stored program selected from memory 52 based on the determined sleep stage, a stored therapy program and instructions indicating modifications to be made to a stored therapy program based on the determined sleep stage, a stored therapy program that has already been modified, or indicators associated with any of the aforementioned therapy programs (e.g., alphanumeric indicators associated with the therapy program). In some examples, processor 50 may record information relating to the sleep stage indication, e.g., the date and time of the particular patient state, in memory 52 for later retrieval and analysis by a clinician.

Processor 50 controls telemetry module 56 to send and receive information. Telemetry module 56 in IMD 16, as well as telemetry modules in other devices and systems described herein, such as programmer 14, may accomplish communication by RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request from IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
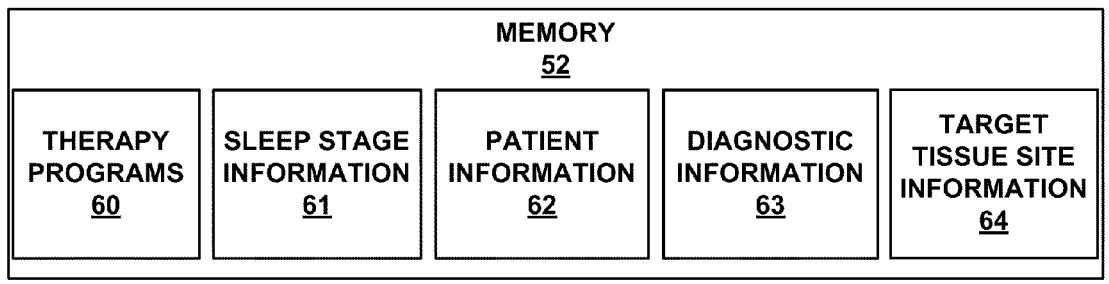
FIG. 3 is a functional block diagram illustrating an example configuration of a memory of a medical device.

FIG. 3 is a block diagram illustrating an example configuration of memory 52 of IMD 16. In the example of FIG. 3, memory 52 stores therapy programs 60, sleep stage information 61, patient information 62, diagnostic information 63, and target tissue site information 64.

Therapy programs 60 may store a plurality of therapy programs as respective records that are stored in a table or other data structure that associates therapy programs or electrical stimulation parameter values with one or more sleep stages (e.g., Stage 1, Stage 2, Deep Sleep or REM) and/or frequency characteristics (e.g., threshold values or templates). While the remainder of the disclosure refers primarily to tables, the present disclosure also applies to other types of data structures that store therapy programs or electrical stimulation parameter values and associated physiological parameters.

In the case of electrical stimulation therapy, each of the programs in therapy programs 60 may include respective values for a plurality of therapy parameters, such as voltage or current amplitude, signal duration, frequency, and electrode configuration (e.g., an indication of the electrodes 22 selected to deliver stimulation and the respective polarity of the electrodes). Processor 50 of IMD 16 may select one or more programs from the stored therapy programs 60 based on a sleep stage determined at least in part based on a biosignal sensed within brain 13 of patient 12. The therapy programs stored in programs 60 may be generated using programmer 14, e.g., during an initial or follow-up programming session, and received by processor 50 from programmer 14 via telemetry module 56. Therapy programs 60 may associate electrical stimulation parameter values or instructions for modifying a baseline therapy program with a particular sleep stage. In this manner, electrical stimulation can be controlled by activation, deactivation, increasing an intensity, or decreasing an intensity of electrical stimulation achieved by selecting a therapy program from the stored therapy programs 60 or selecting instructions for modifying a therapy program.

In other examples, programmer 14 may store programs 60, and processor 50 of IMD 16 may receive selected programs from programmer 14 via telemetry circuit 56. Programmer 14 may allow a user to modify single or multiple parameter values that may or may not be included in a therapy program.

Sleep stage information 61 may store information associating various sleep stage indicators, e.g., biosignals and, in some cases, a physiological signal indicative of a physiological parameter of patient 12 other than brain activity, with a respective sleep stage. For example, sleep stage information 61 may store a plurality of threshold values or templates, where each threshold value or template may correspond to at least one type of sleep stage. The threshold values may be, for example, threshold power levels within selected frequency bands that indicate a particular sleep stage, or values that are generated based on ratios of power between two or more frequency bands. The thresholds may be patient specific or may be generally applicable to more than one patient. The template may be, for example, a waveform template or a pattern in power levels of the biosignal within a selected frequency band over time. Sleep stage detection module 59 may access sleep stage information 61 to determine, based on the threshold values or templates, whether a detected biosignal is indicative of a particular sleep stage. Patient information portion 62 of memory 52 may store data relating to patient 12, such as the patient's name and age, the type of IMD 16 or leads 20 implanted within patient 12, medication prescribed to patient 12, and the like. Processor 50 of IMD 16 may also collect diagnostic information 63 and store diagnostic information 63 within memory 52 for future retrieval by a clinician. Diagnostic information 63 may, for example, include selected recordings of the output of sensing module 55 or sleep stage indications generated by sleep stage module 59. In some examples, diagnostic information 63 may include information identifying the time at which the different sleep stages occurred. A clinician may later retrieve the information from diagnostic information 63 and determine a length of one or more of the patient's sleep stages based on this information.

Diagnostic information 63 may include other information or activities indicated by patient 12 using programmer 14, such as changes in symptoms, medication ingestion, or other activities of patient 12. A clinician may review diagnostic information 63 in a variety of forms, such as timing diagrams or a graph resulting from statistical analysis of diagnostic information 63, e.g., a bar graph. The clinician may, for example, download diagnostic information 63 from IMD 16 via programmer 14 or another computing device. Diagnostic information 63 may also include calibration routines for electrodes 22 (FIG. 1) and malfunction algorithms to identify stimulation dysfunctions.

Target tissue site information 64 may include pre-recorded biosignal signatures, templates or thresholds that correspond to a biosignal sensed within a particular structure or tissue site within patient 12. In some examples, biosignal comparison module 57 of processor 50 may use this stored data to determine a location of lead 20 within patient 12, as discussed above with respect to FIG. 2.

Figure 4:
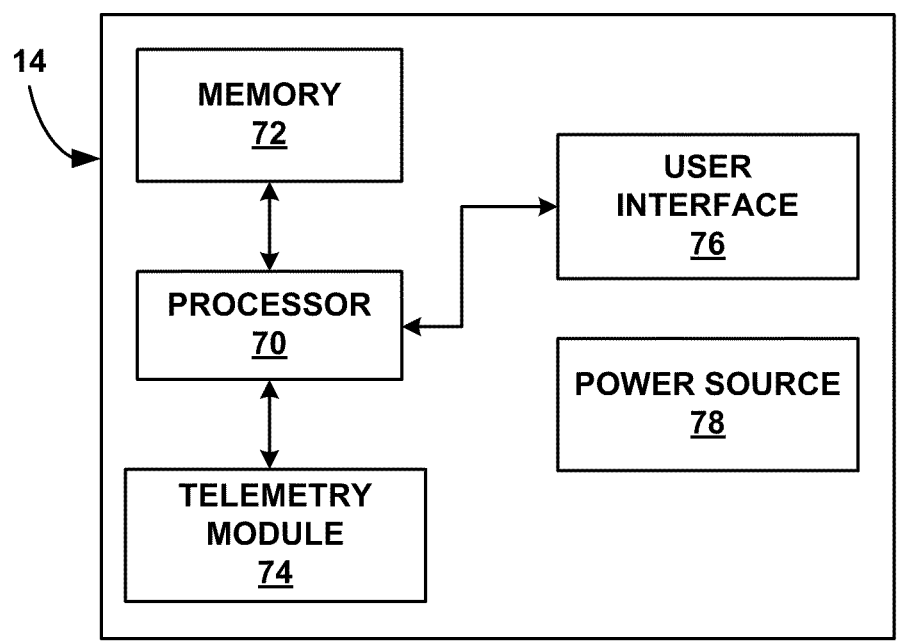
FIG. 4 is a functional block diagram illustrating components of an example medical device programmer.

FIG. 4 is a conceptual block diagram of an example external medical device programmer 14, which includes processor 70, memory 72, telemetry module 74, user interface 76, and power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

Processor 70 monitors activity from the input controls and controls the display of user interface 76. The user, such as a clinician or patient 12, may interact with programmer 14 through user interface 76. User interface 76 may include a display (not shown), such as an LCD or other type of screen, to present information related to the therapy, and input controls (not shown) to provide input to programmer 14. Input controls may include buttons, a keypad (e.g., an alphanumeric keypad), a peripheral pointing device, or another input mechanism that allows the user to navigate though the user interface of programmer 14 and to provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or sounds to patient 12 and/or receiving voice commands from patient 12, which may be useful if patient 12 has limited motor functions.

In some examples, at least some of the control of therapy delivery by IMD 16 may be implemented by processor 70 of programmer 14. For example, in some examples, processor 70 may receive a biosignal from IMD 16 or from a sensing module that is separate from IMD 16, where the biosignal is sensed within brain 13 by IMD 16 or the sensing module that is separate from IMD 16. The separate sensing module may, but need not be, implanted within patient 12. In some examples, processor 70 may determine the current sleep stage of patient 12 based on the detected biosignal and may transmit a signal to IMD 16 via telemetry module 74, to indicate the determined sleep stage. For example, processor 70 may include a sleep stage detection module similar to sleep stage detection module 59 (FIG. 2) of IMD 16. Processor 50 of IMD 16 may receive the signal from programmer 14 via its respective telemetry module 56 (FIG. 3).

Processor 50 of IMD 16 may select one or more stored therapy programs from memory 52 based on the current sleep stage. Alternatively, processor 70 of programmer 14 may select a therapy program and transmit a signal to IMD 16, where the signal indicates the therapy parameter values to be implemented by IMD 16 during therapy delivery to help improve the patient's sleep quality, or may provide an indication of the selected therapy program that is stored within memory 52 of IMD 16. The indication may be, for example, an alphanumeric identifier or symbol that is associated with the therapy program in memory 52 of IMD 16.

In other examples, processor 70 may determine whether lead 20, and, more specifically, electrodes 22 of lead 20, are implanted at the desired target tissue site within brain 13 of patient 12 based on the biosignal detected via IMD 16 or a separate sensing module. For example, processor 70 (or programmer 14) may include a biosignal comparison module similar to biosignal comparison module 57 (FIG. 2) of IMD 16. Processor 70 may transmit a signal to IMD 16 via the respective telemetry modules 74, 56 that indicates electrical stimulation can be delivered to patient 12 because lead 20 is positioned at the target tissue site within brain 13. Alternatively, processor 70 may alert a user via user interface 76 or another interface if lead 20 is not appropriately positioned within patient 12, as determined by analysis of the biosignal. Patient 12, a clinician or another user may also interact with programmer 14 to manually select therapy programs, generate new therapy programs, modify therapy programs through individual or global adjustments, and transmit the new programs to IMD 16. In a learning mode, programmer 14 may allow patient 12 and/or the clinician to determine which therapy programs are best suited for one or more specific sleep stages and for the awake patient state.

Memory 72 may include instructions for operating user interface 76, telemetry module 74 and managing power source 78. Memory 72 may also store any therapy data retrieved from IMD 16 during the course of therapy. The clinician may use this therapy data to determine the progression of the patient condition in order to predict future treatment. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to telemetry module 56 of IMD 16. In alternative examples, programmer 14 may be capable of infrared communication or direct communication through a wired connection. In this manner, other external devices may be capable of communicating with programmer 14 without needing to establish a secure wireless connection.

Power source 78 delivers operating power to the components of programmer 14. Power source 78 may include a battery and a power generation circuit to produce the operating power. In some examples, the battery may be rechargeable to allow extended operation. Recharging may be accomplished electrically coupling power source 78 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 78 may include circuitry to monitor power remaining within a battery. In this manner, user interface 76 may provide a current battery level indicator or low battery level indicator when the battery needs to be replaced or recharged. In some cases, power source 78 may be capable of estimating the remaining time of operation using the current battery.

In some examples, processor 70 of programmer 14 or processor 50 of IMD 16 may monitor another physiological parameter of patient 12 in addition to the bioelectrical brain signal to confirm that patient 12 is in a sleep state or in a determined sleep stage. Examples of physiological parameters that may indicate a sleep state or sleep stage include, for example, activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response.

In some examples, processor 50 of IMD 16 or another device may confirm that patient 12 is asleep based on a physiological parameter of patient 12 other than bioelectrical brain signals or the biosignal (i.e., the bioelectrical brain signal) prior to initiating therapy delivery to the substantia nigra and/or subthalamic nucleus of patient 12 to help improve the patient's sleep quality. In one example, processor 50 of IMD 16 may determine values of one or more sleep metrics that indicate a probability of a patient being asleep based on the current value of one or more physiological parameters of the patient, as described in commonly-assigned U.S. Patent Application Publication No. 2005/0209512 by Heruth et al., entitled "DETECTING SLEEP," which was filed on Apr. 15, 2004. U.S. Patent Application Publication No. 2005/0209512 is incorporated herein by reference in its entirety.

As described in U.S. Patent Application Publication No. 2005/0209512, a sensor that is incorporated with IMD 16, or, in some examples, a separate sensor, may generate a signal as a function of at least one physiological parameter of a patient that may discernibly change when the patient is asleep. Examples of physiological parameters that may indicate a sleep stage include, for example, activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In some examples, processor 50 of IMD 16 may determine a value of a sleep metric that indicates a probability of the patient being asleep based on a physiological parameter. In particular, processor 50 (or processor 70 of programmer 14) may apply a function or look-up table to the current value and/or variability of the physiological parameter to determine the sleep metric value. Processor 50 may compare the sleep metric value to a threshold value to determine whether the patient is asleep. In some examples, the probability may be more than just an indication of "sleep state" or "awake state" but may include an indication of the probability, e.g., between 1% to about 100%, that patient 12 is in a sleep state.

Due to the proximity of the substantia nigra and the subthalamic nucleus within brain 13 of patient 12, a common lead can deliver electrical stimulation to both the substantia nigra and the subthalamic nucleus. The use of one lead to independently deliver stimulation to the substantia nigra and the subthalamic nucleus can provide certain advantages, such as minimizing the invasiveness of DBS system 10. In addition, in some examples, electrodes 22 are arranged on lead 20 (e.g., axially spaced from each other along the longitudinal axis of lead 20) such that once the subthalamic nucleus is located by sensing biosignals with electrodes 22A, there is a high likelihood that electrodes 22B are properly positioned in the substantia nigra. In other examples, electrodes 22 are arranged on lead 20 such that once substantia nigra 22B is located by sensing biosignals with electrodes 22B, there is a high likelihood that electrodes 22A are properly positioned in the subthalamic nucleus.

Figure 5A:
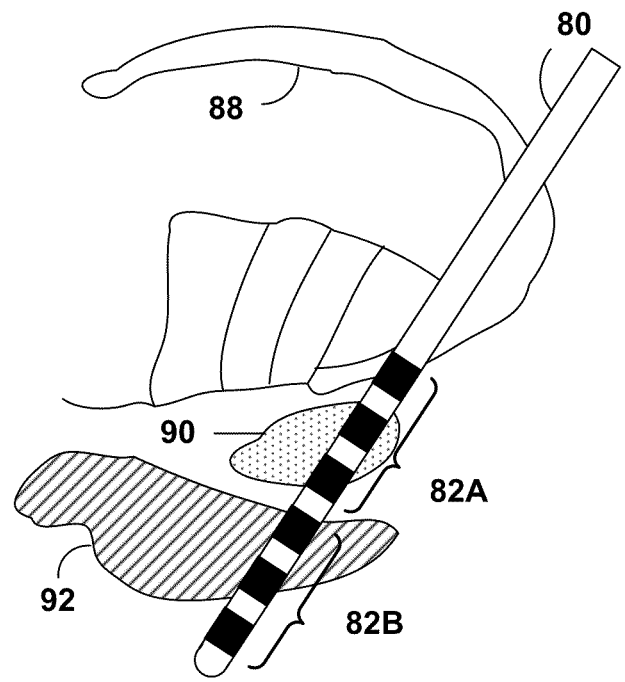
FIG. 5A is a diagram illustrating an example medical lead comprising electrodes that are arranged to stimulate the substantia nigra and the subthalamic nucleus.
Figure 5B:
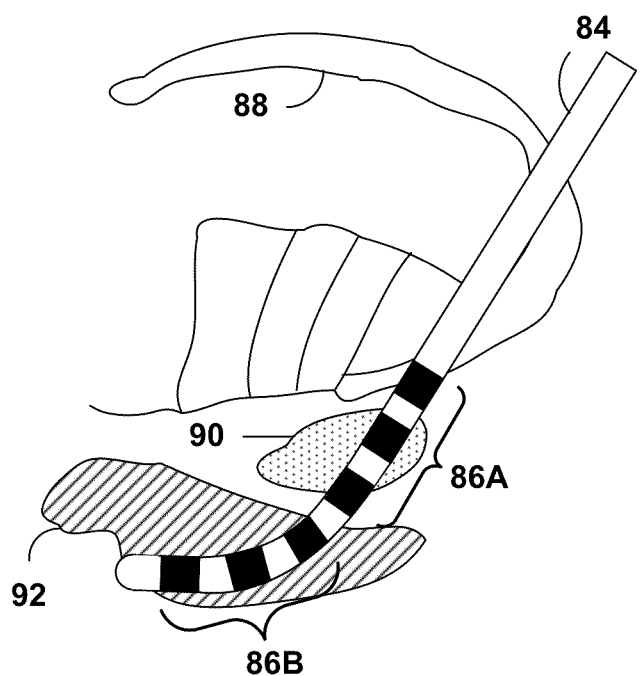
FIG. 5B is a diagram illustrating another example medical lead comprising electrodes that are arranged to stimulate the substantia nigra and the subthalamic nucleus.

FIGS. 5A and 5B are conceptual diagrams illustrating example configurations of lead 20 of FIG. 1. FIG. 5A illustrates an example lead 80 that has a relatively straight configuration, such that a longitudinal axis of lead 80 defines a substantially straight line. Lead 80 includes sets of electrodes 82A and 82B (collectively "electrodes 82"), which may be examples of electrodes 22 shown in FIGS. 1 and 2, which are configured to deliver electrical stimulation to subthalamic nucleus 90 and substantia nigra 92, respectively, of brain 13 of patient 12. As shown in FIGS. 5A and 5B, subthalamic nucleus 90 and substantia nigra 92 are located proximate (e.g., posterior to) thalamus 88 of brain 13 of patient 12.

FIG. 5B illustrates an example lead 84 that has a curvilinear configuration, such that a lead 80 defines a substantially curvilinear profile. Lead 84 includes sets of electrodes 86A and 86B (collectively "electrodes 86"), which may be examples of electrodes 22 of FIGS. 1 and 2. Electrodes 86A, 86B are configured to deliver electrical stimulation to subthalamic nucleus 90 and substantia nigra 92, respectively, of brain 13 of patient 12. In some examples, lead 84 may be relatively straight when implanted within brain 13, but may attain the curvilinear configuration after implantation in brain 13. For example, lead 84 may have elastic properties or may be formed of a shape memory metal that changes from a first shape (e.g., linear or having a greater radius of curvature) to the curvilinear shape shown in FIG. 5B after implantation in patient 12. In some cases, a restraining member such as a stylet or an introducer lumen can help lead 84 maintain the first shape until the second shape is desirable.

As previously mentioned, electrical stimulation of subthalamic nucleus 90 and substantia nigra 92 may provide effective therapy for a sleep disorder of patient 12. Simultaneously but independently controlling electrical stimulation of both subthalamic nucleus 90 and substantia nigra 92 may result in increased quality of sleep for patient 12. Substantia nigra 92 may play a role in sleep regulation and subthalamic nucleus 90 may play a role in movement control. In FIGS. 5A and 5B, electrodes 82 and 86 may be positioned such that electrodes 82A and 86A deliver electrical stimulation to subthalamic nucleus 90 in order to effectively treat sleep disorder symptoms associated with movement control and electrodes 82B and 86B may deliver electrical stimulation to substantia nigra 92 in order to effectively treat sleep disorder symptoms associated with sleep regulation. Controlling delivery of electrical stimulation to both subthalamic nucleus 90 and substantia nigra 92 based on a particular sleep stage may more effectively treat the symptoms of patient 12.

While delivery of stimulation to subthalamic nucleus 90 via electrodes 82A and 86A may result in incidental stimulation to substantia nigra 92, the incidental stimulation may not have a sufficient intensity to generate physiological effects. That is, delivery of stimulation to subthalamic nucleus 90 via electrodes 82A and 86A may generate an electrical field that covers at least a part of substantia nigra 92, but the portion of the electrical field that overlaps with substantia nigra 92 may be insufficient to activate the neurons within substantia nigra 92. In addition, delivery of stimulation to substantia nigra 92 via electrodes 82B and 86B may result in incidental stimulation to subthalamic nucleus 90, but the incidental stimulation may not be of sufficient intensity to generate physiological effects. The delivery of stimulation to substantia nigra 92 via electrodes 82B and 86B may generate an electrical field that covers at least a part of subthalamic nucleus 90, but the portion of the electrical field that overlaps with subthalamic nucleus 90 may be insufficient to activate the neurons within subthalamic nucleus 90.

Electrical stimulation of both subthalamic nucleus 90 and substantia nigra 92 using a single lead 80 or 84 may be facilitated by the close proximity of subthalamic nucleus 90 and substantia nigra 92 to one another, as illustrated in the schematic figures shown in FIGS. 5A and 5B. Subthalamic nucleus 90 lies just dorsal to substantia nigra 92. As can be seen in FIGS. 5A and 5B, one lead (e.g., lead 80 or 84) may be inserted into brain 13 so that different electrodes of the same lead may be located proximate to both subthalamic nucleus 90 and substantia nigra 92. In other examples, however, multiple leads can be used to deliver stimulation to subthalamic nucleus 90 and substantia nigra 92. For example, separate leads can deliver stimulation to a respective one of the subthalamic nucleus 90 and substantia nigra 92, whereby the separate leads can be coupled to a common IMD 16 or separate IMDs. In addition, in some examples, one or more self-contained medical devices (e.g., a microstimulator) that includes electrodes on an outer housing of the medical device can be used to deliver stimulation to subthalamic nucleus 90 to manage a movement disorder of patient 12 and substantia nigra 92 to manage a sleep disorder of patient 12.

Substantia nigra 92 of brain 13 of patient 12 may be directly involved in sleep regulation. Substantia nigra 92 receives input from lateral hypothalamic neurons, located in the hypothalamus (not shown) of brain 13, which may regulate the alteration between brain states associated with sleep, wake, arousal, and movement. Delivery of electrical stimulation to substantia nigra 92 via electrodes 82B or 86B may increase the ability of brain 13 to regulate the sleep-wake cycle of patient 12 (e.g., to initiate or maintain a particular sleep stage) by modulating the excitability of substantia nigra 92 by the lateral hypothalamic neurons. Therefore, delivery of stimulation to substantia nigra 92 during the Stage 1, Stage 2, Deep Sleep, and/or REM sleep stages can be useful to improve the sleep quality of patient 12.

In addition, Parkinson's disease or another neurological disorder may cause patient 12 to have difficulty moving or controlling movement during a particular sleep stage. For example, an inability to move during the Stage 1 sleep stage, when patient 12 is attempting to initiate sleep, may be discomforting to patient 12, which may affect the ability of patient 12 to fall asleep. Accordingly, during a sleep stage associated with the Stage 1 sleep stage, delivery of electrical stimulation to subthalamic nucleus 90 via electrodes 82A or 86A may improve the motor skills of patient 12, such that patient 12 may initiate movement or maintain movement, e.g., to adjust a sleeping position. As another example, patient 12 may become more physically active during the REM sleep stage. Patient 12 may involuntarily move his legs during the REM sleep stage or have other periodic limb movements. The physical activity of patient 12 may be disruptive to the patient's sleep, as well as to others around patient 12 when patient 12 is in the REM sleep stage. Accordingly, upon detecting a sleep stage associated with the REM sleep stage, delivery of electrical stimulation to subthalamic nucleus 90 via electrodes 82A or 86A may minimize the movement of patient 12 or allow patient 12 to control movement. However, in other examples, withholding the delivery of stimulation to subthalamic nucleus 90 during the REM sleep stage may also help minimize patient movement during the REM sleep stage, which may help increase the quality of the patient's sleep.

In some examples, IMD 16 does not deliver stimulation to subthalamic nucleus 90 during the Stage 2 and/or Deep Sleep sleep stages of patient 12. In other examples, IMD 16 delivers stimulation to subthalamic nucleus 90 during the Stage 2 and/or Deep Sleep sleep stages of patient 12, but with a lower intensity relative to the stimulation delivered to subthalamic nucleus 90 during the Stage 1 and REM sleep stages. As previously indicated, the lower intensity may be defined by a threshold voltage amplitude, a threshold current amplitude, a threshold frequency, a threshold pulse width or another threshold signal characteristic.

FIG. 6 is a flow diagram illustrating an example technique for controlling delivery of electrical stimulation by IMD 16 based on a determination of a sleep stage of patient 12. While FIG. 6 is described with reference to processor 50 of IMD 16, in other examples, a processor of another device, such as processor 70 of programmer 14 or a processor of a sleep stage detection module that is separate from IMD 16, may control delivery of electrical stimulation by IMD 16 in accordance with the techniques described herein.

Processor 50 may determine whether patient 12 is in a sleep state (100) using any suitable technique. For example, patient 12 may provide input to programmer 14 via user interface 76 indicating that patient 12 is initiating a sleep state (i.e., attempting to sleep). Patient 12 may also provide volitional cues indicating a beginning of a sleep state by providing input via a motion sensor, which then transmits a signal to processor 50. For example, patient 12 may tap a motion sensor in a different pattern to indicate patient 12 is in a sleep state. As other examples, processor 50 may automatically determine patient 12 is in a sleep state by detecting a brain signal within brain 13 that is associated with a volitional patient input, where the brain signal is unrelated to the patient's symptoms or incidentally generated as a result of the patient's condition. Examples of volitional patient inputs are described in U.S. Patent Application Publication No. 2009/0082829 by Panken et al., entitled "PATIENT DIRECTED THERAPY CONTROL," which was filed on Oct. 16, 2007 and is incorporated herein by reference in its entirety.

In another example, processor 50 may detect the sleep state based on values of one or more sensed patient parameters. For example, processor 50 may detect when patient 12 is sitting or lying down based on a motion sensor or an accelerometer that indicates patient posture and determine patient 12 is in a sleep state upon detecting a relatively low activity level. In another example, processor 50 may detect the sleep state based on values of one or more sleep metrics that indicate a probability of patient 12 being asleep, such as using the techniques described in U.S. Patent Application Publication No. 2005/0209512 or in U.S. Pat. No. 7,491,181 issued to Heruth et al. on Feb. 17, 2009, entitled "COLLECTING ACTIVITY AND SLEEP QUALITY INFORMATION VIA A MEDICAL DEVICE," which was filed on Apr. 15, 2004 and is incorporated herein by reference its entirety. The sleep metrics may be based on physiological parameters of patient 12, such as activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response.

As described in U.S. Patent Application Publication No. 2005/0209512, processor 50 may apply a function or lookup table to the current value and/or variability of the physiological parameter to determine the sleep metric value and compare the sleep metric value to a threshold value to determine whether patient 12 is asleep. In some examples, processor 50 may compare the sleep metric value to each of a plurality of thresholds to determine the current sleep stage of patient 12, which may then be used to control delivery of electrical stimulation in addition to the sleep stage determination based on the frequency band characteristic of the biosignal monitored within brain 13.

In addition to or instead of detecting a sleep state based on patient input or a physiological parameter of patient 12, processor 50 may detect the sleep state (100) based on a time schedule, which may be stored in memory 52 of IMD 16. The schedule may be selected by a clinician or IMD 16 may learn the schedule based on past patient inputs or other determinations. The schedule may set forth the times of a day in which patient 12 is typically in an awake state (e.g., not in a sleep state) and/or in a sleep state. For example, the schedule may be generated based on a circadian rhythm that is specific to patient 12. Processor 50 may track the time of day with a clock, which may be included as part of processor 50 or as a separate component within IMD 16. In some examples, processor 50 may automatically implement a clock based on a circadian rhythm of a typical patient, i.e., a generic circadian rhythm, rather than a circadian rhythm that is specific to patient 12.

In examples in which processor 50 detects a sleep state (100) based on a predetermined schedule, processor 50 may detect a sleep state at a first time (e.g., 10:00 p.m.) each night based on the schedule (or another time each night). Processor 50 may determine that the sleep state begins at the first time, at which time processor 50 may begin determining the patient sleep stage, as shown in FIG. 6, and ends at a second time (e.g., 8 a.m.), at which time processor 50 may revert to a different therapy control system or control stimulation generator 54 (FIG. 2) to deliver therapy to patient 12 according to a different therapy program (e.g., a therapy program that provides efficacious therapy to patient 12 in the awake state). The therapy control system that provides therapy when patient 12 is awake may, for example, provide substantially continuous therapy to patient 12 or provide therapy to patient 12 upon the detection of movement or upon detection of an intent to move.

After detecting patient 12 is in a sleep state (100), processor 50 receives a biosignal indicative of activity within brain 13 of patient 12 (102), e.g., from sensing module 55 (FIG. 2) or a separate sensing module that senses the biosignal within brain 13 of patient 12. Sleep stage detection module 59, or, more generally, processor 50, may determine a frequency characteristic of the biosignal (104). In some examples, processor 50 may receive the biosignal prior to determining the sleep state. Thus, the technique shown in FIG. 6 is not limited to receiving the biosignal after detecting the sleep state (100). In some examples, processor 50 may continuously receive the biosignal (102) from sensing module 55 or at periodic intervals, which may be set by a clinician. For example, processor 50 may periodically interrogate sensing module 55 to receive the biosignal (102). As another example, sensing module 55 may periodically transmit the biosignal to processor 50, such as at a frequency of about 0.1 Hz to about 100 Hz.

In the example shown in FIG. 6, sleep stage detection module 59 determines a sleep stage of patient based on a frequency band characteristic of the biosignal that is indicative of activity within brain 13 of patient 12. An example technique for determining a sleep stage of patient based on a frequency band characteristic of the biosignal is described in U.S. Patent Application Publication No. 2009/0192556 by Wu et al. (published on Jul. 30, 2009), which is entitled, "SLEEP STAGE DETECTION" and is incorporated herein by reference in its entirety.

Sleep stage detection module 59 (FIG. 2) may determine a frequency band characteristic of the biosignal (104) using any suitable technique. The frequency characteristic may include, for example, at least one of a power level (or energy) within one or more frequency bands of the biosignal, a ratio of the power level in two or more frequency bands, a correlation in change of power between two or more frequency bands, or a pattern in the power level of one or more frequency bands over time. In one example, sleep stage detection module 59 may comprise an amplifier that amplifies a received biosignal and a bandpass or a low pass filter that filters the monitored biosignal to extract one or more selected frequency bands of the biosignal. The extracted frequency bands may be selected based on the frequency band that is revealing of the one or more sleep stages that are being detected. Sleep stage detection module 59 may then determine the frequency characteristic based on the extracted frequency band component of the biosignal.

As described in U.S. Patent Application Publication No. 2009/0192556 by Wu et al., different frequency bands are associated with different activity in brain 13. It is believed that some frequency band components of a biosignal from within brain 13 may be more revealing of particular sleep stages than other frequency components. One example of the frequency bands is shown in Table 2:

TABLE 2

| Frequency bands | |
| --- | --- |
| Frequency (f) Band Hertz (Hz) | Frequency Information |
| f < 5 Hz | δ (delta frequency band) |
| 5 Hz ≤ f ≤ 10 Hz | α (alpha frequency band) |

TABLE 2-continued

| Frequency bands | |
| --- | --- |
| Frequency (f) Band Hertz (Hz) | Frequency Information |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 2 are merely examples. The frequency ranges may differ in other examples. For example, another example of frequency ranges for frequency bands are shown in Table 3:

TABLE 3

| Frequency bands | |
| --- | --- |
| Frequency (f) Band Hertz (Hz) | Frequency Information |
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

Processor 50 may select a frequency band for determining the patient sleep stage using any suitable technique. In one example, the clinician may select the frequency band based on information specific to patient 12 or based on data gathered from more than one patient 12. The frequency bands that are useful for distinguishing between two or more different patient sleep stages or otherwise determining a patient sleep stage based on a biosignal from brain 13 may differ between patients. In some examples, a clinician may calibrate the frequency ranges to a specific patient based on, for example, a sleep study. During the sleep study, the clinician may monitor a biosignal and determine which, if any, frequency bands or ratio of frequency bands exhibit a characteristic that helps to detect a sleep stage and/or distinguish between different sleep stages.

Sleep stage detection module 59 (FIG. 2) may determine a sleep stage based on the frequency characteristic of the biosignal (106). In some techniques, sleep stage detection module 59 may compare the frequency characteristic to one or more threshold values in order to determine the sleep stage or a sleep stage group that includes more than one sleep stage and is associated with a common therapy program. In other examples, sleep stage detection module 59 may compare a trend in the power level within a frequency band of the biosignal over time to a template in order to determine the sleep stage.

After determining a sleep stage of patient 12 (106), processor 50 independently controls therapy delivery to subthalamic nucleus 90 and substantia nigra 92 based on the determined sleep stage (108). For example, processor 50 controls stimulation generator 54 (FIG. 2) to deliver stimulation to subthalamic nucleus 90 and substantia nigra 92 using the technique shown in FIG. 7, which is described in further detail below. In some examples, processor 50 controls therapy delivery to subthalamic nucleus 90 and substantia nigra 92 by selecting respective therapy programs based on the determined sleep stage, e.g., using the therapy programs 60 stored in memory 52 (FIGS. 3 and 4). In other examples, processor 50 may control therapy delivery by modifying a therapy program stored in memory 52 of IMD 16 (FIG. 2) based on the determined sleep stage.

Processor 50 may also determine whether the sleep state has ended (110) in order to, for example, revert to a different therapy program or revert to a different technique for controlling delivery of electrical stimulation by IMD 16 when patient 12 is awake. In some examples, processor 50 may use techniques similar to those described above with respect to detecting the sleep state in order to determine whether the sleep state has ended. For example, patient 12 may provide input to programmer 14 indicating that the present patient state is an awake state and processor 70 of programmer 14 may transmit a signal to processor 50 to indicate that the sleep state has ended. In other examples, processor 50 may determine patient 12 is in an awake state based on the monitored biosignal and/or monitored physiological parameter values, such as a patient posture or activity level, as well as other physiological parameters.

If the sleep state has ended, processor 50 may stop detecting the patient sleep stage until the sleep state is detected again (100). If the sleep state has not ended, processor 50 may continue to monitor the biosignal from brain 13 (102) and continue to determine a sleep stage based on a frequency characteristic of the biosignal (104, 106) in order to control therapy (108).

Figure 7:
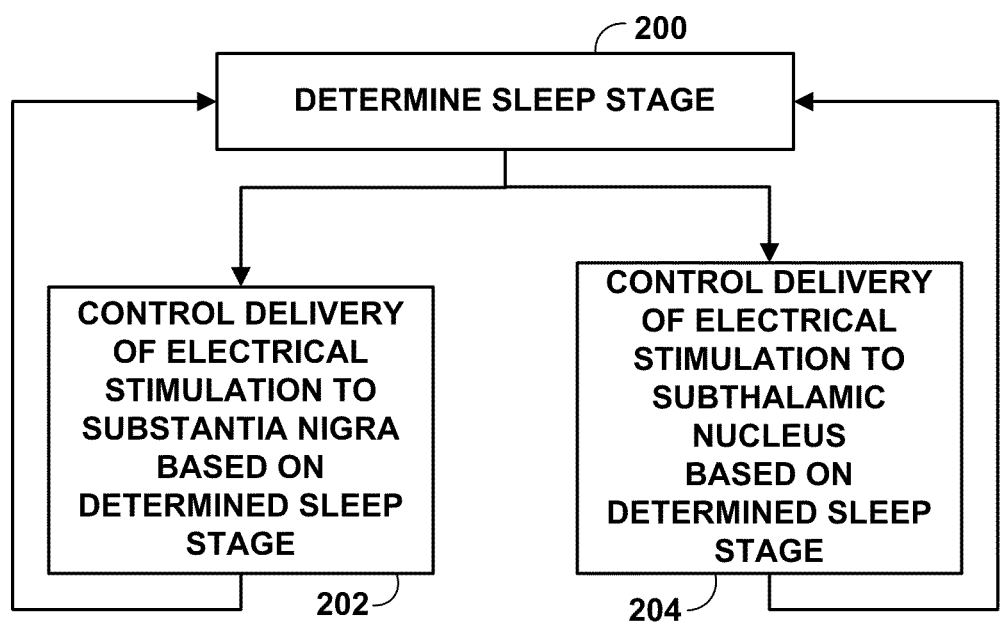
FIGS. 7 and 8 are flow diagrams illustrating example techniques for controlling therapy delivery to the subthalamic nucleus and substantia nigra of a patient based on a determined patient sleep stage.

FIG. 7 is a flow diagram illustrating an example technique for controlling delivery of electrical stimulation to, for example, subthalamic nucleus 90 and substantia nigra 92 of brain 13 of patient 12 based on the determined sleep stage of patient 12. As discussed with respect to FIG. 6, sleep stage detection module 59 of processor 50 (FIG. 2) determines the current sleep stage of patient 12, e.g., based on a bioelectrical brain signal sensed by sensing module 55 (FIG. 2) within brain 13 of patient 12 (200). Based on the determined sleep stage, processor 50 controls stimulation generator 54 (FIG. 2) of IMD 16 to deliver electrical stimulation to substantia nigra 92 of patient 12 (202) and/or subthalamic nucleus 90 of brain 13 of patient 12 (204) via, for example, electrodes 22 of lead 20 (FIGS. 1 and 2). Processor 50 may activate electrical stimulation, deactivate electrical stimulation, increase an intensity of electrical stimulation, or decrease an intensity of electrical stimulation delivered to substantia nigra 92 and subthalamic nucleus 90 based on the determined sleep stage.

Figure 8:
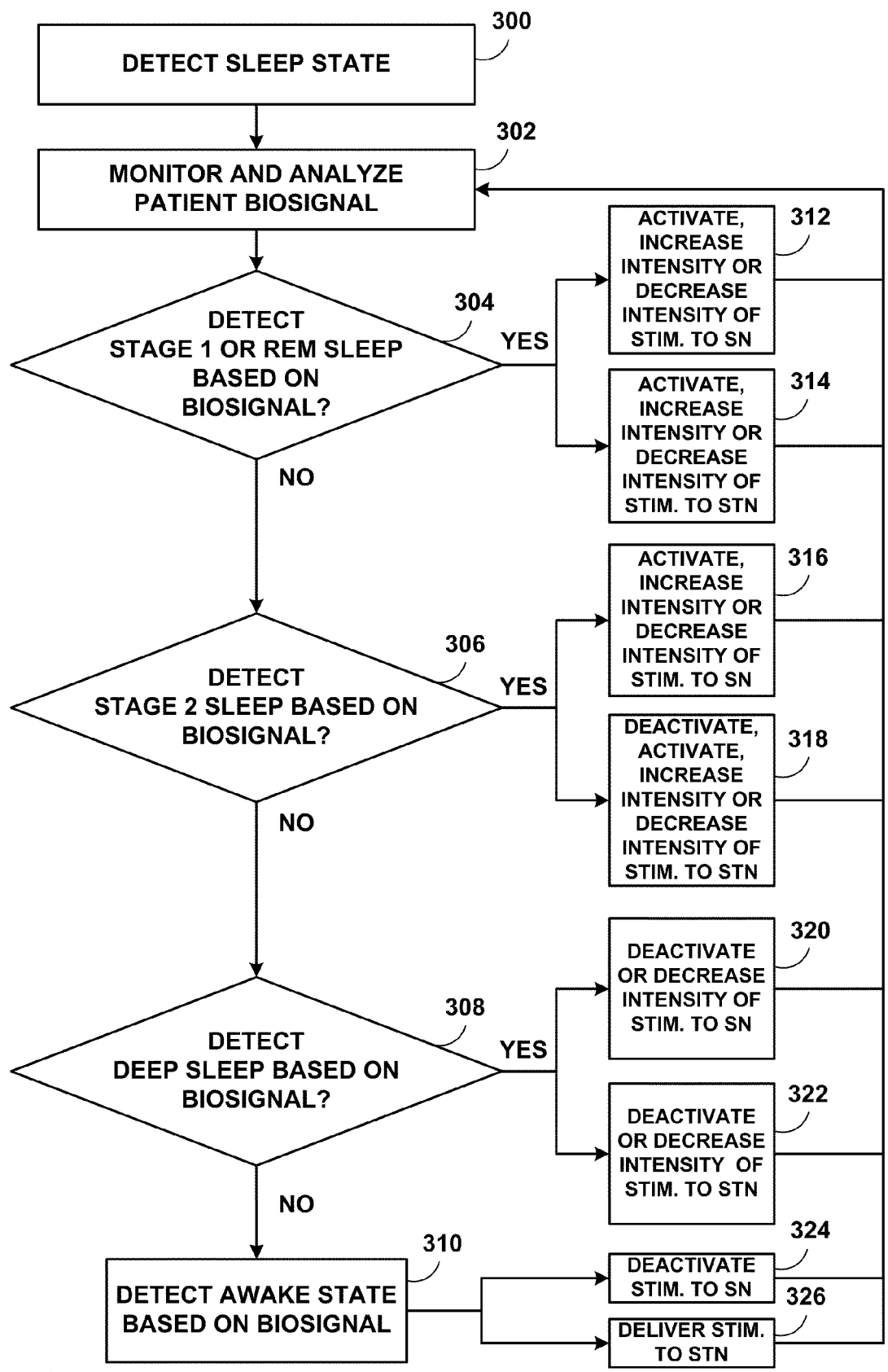

For example, as discussed in further detail with respect to FIG. 8, if sleep stage detection module 59 determines that patient 12 is in a Stage 2 sleep stage, processor 50 controls electrical stimulator 54 to deliver electrical stimulation to substantia nigra 92 in order to maintain the sleep stage. In some examples, processor 50 controls electrical stimulator 54 to deliver electrical stimulation to subthalamic nucleus 90 in order to control the symptoms of the sleep disorder associated with movement during the Stage 2 sleep stage. In other examples, however, such s when the Stage 2 sleep stage of patient 12 naturally involves almost no involuntary movement, and processor 50 controls electrical stimulator 54 to deactivate or minimize the stimulation delivered to subthalamic nucleus 90, e.g., compared to the stimulation delivered during the Stage 1 or REM sleep stages. Thus, if sleep stage detection module 59 determines that patient 12 is in the Stage 2 sleep stage, processor 50 may activate, increase an intensity, or decrease an intensity of electrical stimulation delivered to substantia nigra 92 and activate, deactivate, increase an intensity or decrease an intensity of electrical stimulation delivered to subthalamic nucleus 90 based on the sleep stage determined by sleep stage detection module 59 (i.e., Stage 2).

In general, processor 50 controls stimulation generator 54 to activate stimulation therapy to substantia nigra 92 and subthalamic nucleus 90, deliver therapy to substantia nigra 92 and subthalamic nucleus 90 according to a modified therapy program relative to a previously implemented therapy program, or deactivate stimulation therapy to substantia nigra 92 and subthalamic nucleus 90 based on the determined sleep stage. Processor 50 may independently select a particular therapy program to be delivered to substantia nigra 92 and a different therapy program to be delivered to subthalamic nucleus 90 based on the determined sleep stage. The therapy programs may be delivered simultaneously or alternatively.

FIG. 8 is a flow diagram illustrating an example technique for controlling delivery of electrical stimulation based on a determined sleep stage of patient 12. Patient 12 may, at any time, be in one of an awake state or a sleep state. The sleep state may refer to a state in which patient 12 is intending on sleeping (e.g., initiating thoughts of sleep), is attempting to sleep, or has initiated sleep and is currently sleeping. Upon detecting a sleep state of patient 12 (300), processor 50 monitors a biosignal of patient 12, e.g., based on a signal generated by sensing module 55 (FIG. 2) of IMD 16, and analyzes the biosignal to determine the sleep stage of patient 12 (302).

During the Stage 1 sleep stage, patient 12 may be in the beginning stages of sleep and may begin to lose conscious awareness of the external environment. During the REM sleep stage, patient 12 may exhibit increased heart rate and respiration. In these sleep stages, patient 12 may require electrical stimulation configured to assist patient 12 in initiating sleep or maintaining a sleep stage with relatively more brain activity than the Stage 2 or Deep Sleep sleep stages. Thus, during the Stage 1 sleep stage, processor 50 can control electrical stimulator 54 (FIG. 2) to deliver stimulation to substantia nigra (SN) 112 of brain 13 of patient 12 in order to regulate the sleep-wake cycle. In addition, because patient 12 may naturally undergo more motor activity during the Stage 1 and REM sleep stages compared to the Stage 2 and Deep Sleep sleep stages, processor 50 can control stimulation generator 54 to deliver electrical stimulation to subthalamic nucleus (STN) 90 of patient 12. For example, if sleep stage detection module 59 determines that patient 12 is in either the Stage 1 or REM sleep stages (304), processor 50 may activate, increase an intensity, or decrease an intensity of electrical stimulation delivered to substantia nigra 92 (312) and subthalamic nucleus 90 at 314 based on the determined sleep stage e.g., Stage 1 or REM (314).

Whether processor controls stimulation generator 54 to activate, increase an intensity, or decrease an intensity of electrical stimulation depends upon the intensity of the stimulation therapy that was delivered prior to detecting the Stage 1 sleep stage. In general, if no stimulation therapy was delivered prior to the detection of the Stage 1 or REM sleep stages, processor 54 controls stimulation generator 54 to activate stimulation therapy to the substantia nigra 92 and subthalamic nucleus 112. If stimulation therapy was being delivered prior to the detection of the Stage 1 or REM sleep stages at an intensity that is less than that desirable (e.g., as indicated by a voltage or current amplitude, frequency, pulse width, and/or other signal characteristic that is less than a threshold value) for the Stage 1 and REM sleep stages, processor 54 controls stimulation generator 54 to increase the intensity of stimulation upon detection of the Stage 1 or REM sleep stages (304). On the other hand, if stimulation therapy was being delivered prior to the detection of the Stage 1 or REM sleep stages at an intensity that is greater than that desirable (e.g., as indicated by a voltage or current amplitude, frequency, pulse width, and/or other signal characteristic that is greater than a threshold value) for the Stage 1 and REM sleep stages, processor 54 controls stimulation generator 54 to decrease the intensity of stimulation upon detection of the Stage 1 or REM sleep stages (304).

For example, if patient 12 has just entered the Stage 1 sleep stage for the first time during a sleep state, processor 50 may not necessarily decrease an intensity of electrical stimulation delivered to substantia nigra 92 because no previous delivery of electrical stimulation to substantia nigra 92 may have occurred. However, because patient 12 may cycle through the sleep stages, patient 12 may be in a sleep stage other than Stage 1 prior to re-entering the Stage 1 sleep stage. Thus, the ability of processor 50 to decrease an intensity of electrical stimulation in response to determining that patient 12 is in Stage 1 sleep may be necessary in order for stimulation generator 54 of IMD 16 to deliver the appropriate amount of stimulation therapy to patient 12.

If patient 12 is not in a Stage 1 or REM sleep stage at 304, sleep stage detection module 59 may determine whether patient 12 is in a Stage 2 sleep stage (306). As previously discussed, during the Stage 2 sleep stage, muscular activity of patient 12 may decrease and conscious awareness of the external environment may disappear. Patient 12 may continue to require adjustment and delivery of electrical stimulation to substantia nigra 92 in order to maintain the sleep stage. During the Stage 2 sleep stage, patient 12 may also exhibit relatively less motor activity than during the Stage 1 or REM sleep stages but relatively more motor activity than during the Deep Sleep sleep stage. Consequently, patient 12 may continue to require delivery and adjustment of electrical stimulation to subthalamic nucleus 90 in order to control the symptoms of the sleep disorder associated with movement. However, with some patients, the Stage 2 sleep stage may naturally involve almost no movement, and, therefore, in some examples, patient 12 may no longer require stimulation of subthalamic nucleus 90 to control difficulty with movement. Thus, if patient 12 is in the Stage 2 sleep stage, in some examples, processor 50 may activate, increase an intensity, or decrease an intensity of electrical stimulation delivered to substantia nigra 92 (316) and activate, deactivate, increase an intensity or decrease an intensity of electrical stimulation delivered to subthalamic nucleus 90 (318) based on the determined sleep stage (i.e., Stage 2).

Again, whether processor 50 controls stimulation generator 54 to activate, deactivate, increase an intensity, or decrease an intensity of electrical stimulation delivered during the Stage 2 sleep stage depends upon the intensity of the stimulation therapy that was previously delivered. If no stimulation therapy was delivered prior to the detection of the Stage 2 sleep stage, processor 54 controls stimulation generator 54 to activate stimulation therapy to the substantia nigra 92 and, in some cases, the subthalamic nucleus 112 in response to detecting the Stage 2 sleep stage (306). If stimulation therapy was being delivered to the substantia nigra 92 and/or subthalamic nucleus 90 prior to the detection of the Stage 2 sleep stage at an intensity that is less than desirable (e.g., as indicated by a voltage or current amplitude, frequency, pulse width, and/or other signal characteristic that is less than a threshold value), processor 54 controls stimulation generator 54 to increase the intensity of stimulation to the substantia nigra 92 and/or subthalamic nucleus 90 upon detection of the Stage 2 (306). On the other hand, if stimulation therapy was being delivered to the substantia nigra 92 and/or subthalamic nucleus 90 prior to the detection of the Stage 2 sleep stage at an intensity that is greater than that desirable (e.g., as indicated by a voltage or current amplitude, frequency, pulse width, and/or other signal characteristic that is greater than a threshold value) for the Stage 2 sleep stage, processor 54 controls stimulation generator 54 to decrease the intensity or deactivate the stimulation delivered to the substantia nigra 92 and/or subthalamic nucleus 90 upon detection of the Stage 2 sleep stage (306).

If patient 12 is not in the Stage 2 sleep stage, sleep stage detection module 59 may determine whether patient 12 is in a Deep Sleep sleep stage (308). As previously mentioned, during the Deep Sleep sleep stage, muscular activity of patient 12 may decrease and conscious awareness of the external environment may disappear. In some examples, patient 12 may require minimal to no stimulation to substantia nigra 92 and subthalamic nucleus 90 to maintain the sleep state. Thus, if stimulation was previously delivered, patient 12 is in the Deep Sleep sleep stage, processor 50 may deactivate therapy delivery or decrease the intensity of electrical stimulation delivered to substantia nigra 92 (320) and subthalamic nucleus 90 (322) based on the determined sleep stage (i.e., Deep Sleep). Alternatively, if therapy was not being delivered previous to the detection of the Deep Sleep state and a relatively low (e.g., as indicated by a threshold amplitude, frequency, pulse width or other stimulation parameter value) stimulation is desirable during the Deep Sleep stage, processor 50 may control stimulation generator 54 to activate and/or increase the intensity of electrical stimulation delivered to substantia nigra 92 and/or subthalamic nucleus during the Deep Sleep stage.

In examples in which no stimulation delivery to the substantia nigra 92 and/or subthalamic nucleus 90 is desirable or necessary during the Deep Sleep sleep stage, processor 50 controls stimulation generator 54 to deactivate the delivery of stimulation to the substantia nigra 92 and/or subthalamic nucleus 90. Whether processor 50 controls stimulation generator 54 to maintain an intensity or decrease an intensity of electrical stimulation delivered during the Deep Sleep sleep stage depends upon the intensity of the stimulation therapy that was previously delivered. If stimulation therapy was being delivered to the substantia nigra 92 and/or subthalamic nucleus 90 prior to the detection of the Deep Sleep sleep stage at an intensity that is less than desirable (e.g., as indicated by a voltage or current amplitude, frequency, pulse width, and/or other signal characteristic that is less than a threshold value), processor 54 controls stimulation generator 54 to increase the intensity of stimulation to the substantia nigra 92 and/or subthalamic nucleus 90 upon detection of the Stage 2 (308). On the other hand, if stimulation therapy was being delivered to the substantia nigra 92 and/or subthalamic nucleus 90 prior to the detection of the Stage 2 sleep stage at an intensity that is greater than that desirable (e.g., as indicated by a voltage or current amplitude, frequency, pulse width, and/or other signal characteristic that is greater than a threshold value) for the Stage 2 sleep stage, processor 54 controls stimulation generator 54 to decrease the intensity or deactivate the stimulation delivered to the substantia nigra 92 and/or subthalamic nucleus 90 upon detection of the Stage 2 sleep stage (308).

In each of the instances in which a sleep stage is detected (302, 304, 309, 308), processor 50 can control stimulation generator 54 to maintain an intensity of stimulation if the stimulation therapy that was delivered to substantia nigra 92 and/or subthalamic nucleus 90 immediately prior to the detection of the particular sleep stage was at the desired stimulation intensity (e.g., stimulation generator 54 was delivering stimulation according to a same or similar therapy program).

If patient 12 is not in the Deep Sleep sleep stage, patient 12 may no longer be in a sleep state, and alternatively may be in an awake state (310). Adjustment or delivery of electrical stimulation to substantia nigra 92 to regulate the sleep of patient 12 may not be necessary if processor 50 determines that patient 12 is in the awake state. However, adjustment or delivery of electrical stimulation to subthalamic nucleus 90 to control symptoms of the movement disorder of patient 12 may continue to be necessary. Thus, if patient 12 is in an awake state, processor 50 may deactivate electrical stimulation to substantia nigra 92 (324) but continue to control delivery of electrical stimulation to subthalamic nucleus 90 (326).

Processor 50 may continue to determine whether patient 12 is in a sleep state (300), and may monitor and analyze a sensed biosignal to determine if the sleep stage or sleep state of patient 12 has changed (302). If a change is detected, processor 50 can modify delivery of electrical stimulation accordingly, as in the technique shown in FIG. 7.

Figure 9:
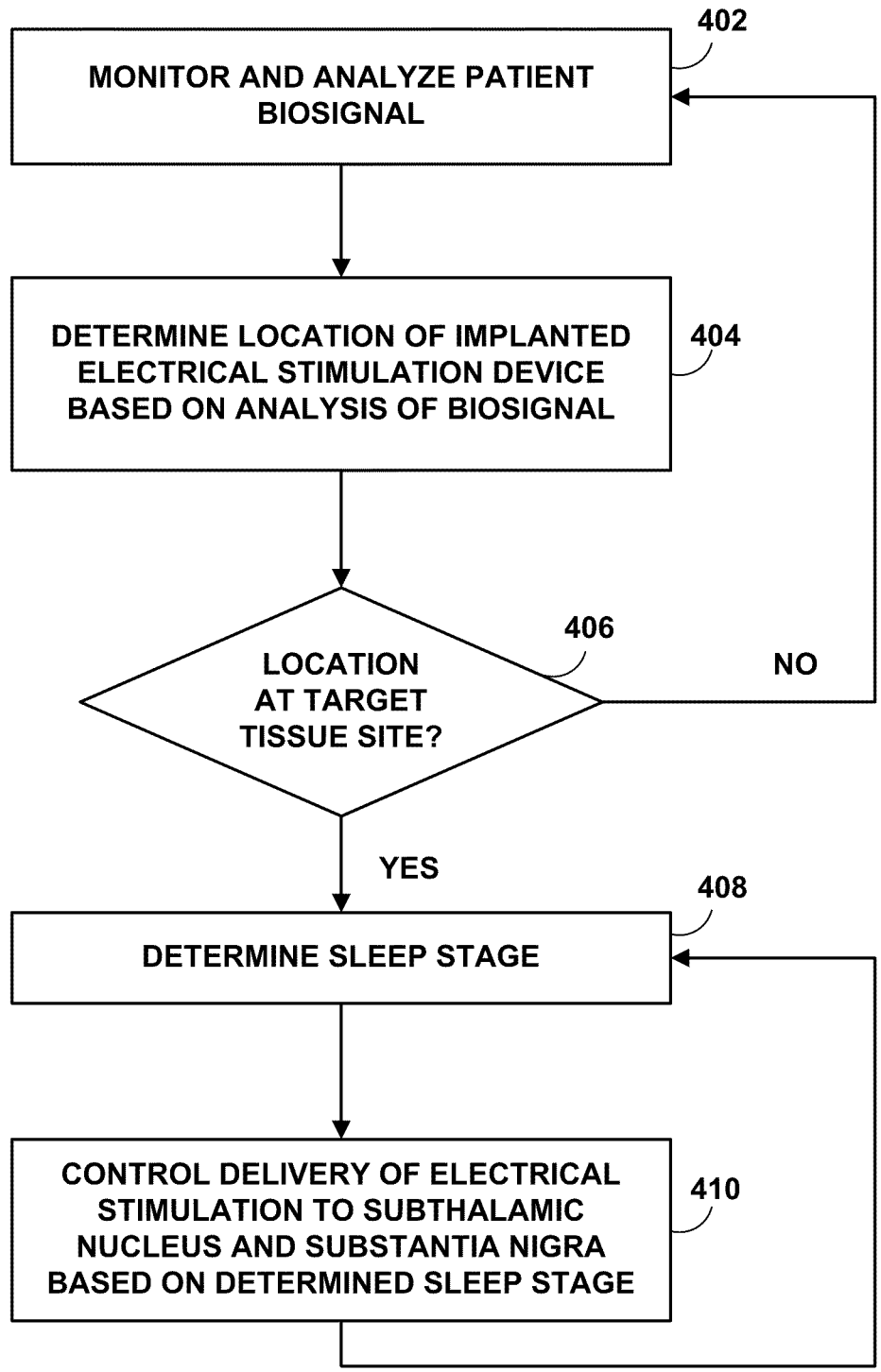
FIG. 9 is a flow diagram illustrating an example technique for determining whether an implanted electrical stimulation device is located at a target tissue site.

FIG. 9 is a flow diagram illustrating an example technique for confirming electrodes 22 are positioned at one or more target tissue sites (e.g., subthalamic nucleus 90 and substantia nigra 92) within brain 13 of patient 12. Part of the technique shown in FIG. 9 can be implemented when lead 20 is implanted within patient 12. In other examples, IMD 16 can perform the technique shown in FIG. 9 in order to, for example, confirm that lead 20 has not migrated and electrodes are positioned at one or more target tissue sites. IMD 16 can periodically perform the technique shown in FIG. 9, e.g., as a part of a regularly scheduled diagnostic test or upon initiation of the technique by patient 12, a clinician or a patient caretaker. For example, a user can interact with programmer 14 when confirmation of the electrode implant site is desired, and programmer 14 can transmit instructions to processor 50 of IMD 16 via respective telemetry modules 74, 56, where the instructions cause processor 50 to begin the test shown in FIG. 9.

After lead 20 (FIGS. 1 and 2) is implanted in brain 13 of patient 12, sensing module 50 can sense a biosignal via one or more electrodes 22 of lead 20 and/or a reference electrode, such as an electrode on an outer housing of IMD 16. As previously mentioned, lead 20 of DBS system 10 may be implanted to position electrodes 22 at a desired location of brain 13 through a hole in cranium 26. Lead 20 may be placed at any location within brain 13 such that electrodes 22 are capable of providing electrical stimulation to target tissue sites within brain 13 during treatment. The clinician may approximate the location of the target tissue sites based on past knowledge of brain anatomy or using an imaging technique, such as, but not limited to, fluoroscopy.

Processor 50 monitors and analyze a biosignal of patient 12 sensed via electrodes 22 of lead 20 (402), and determine the location of electrodes 22 based on analysis of the biosignal (404). Specific biosignals (e.g. local field potentials) of brain 13 may be monitored in order to determine the location of specific structures of brain 13. For example, in patients with Parkinson's disease, substantia nigra 92 may have a higher firing rate (i.e., the neurons may fire at a higher frequency) than subthalamic nucleus 90, and the oscillation of the beta band frequency of the local field potential may be lower in substantia nigra 92 than in subthalamic nucleus 90.

As an example, in patients with Parkinson's disease, the firing rate of signals within subthalamic nucleus 90 may be approximately 20-50 Hz and the firing rate of signals within the substantia nigra 92 may be approximately 90 Hz.

Biosignal comparison module 57 (FIG. 2) can compare a biosignal sensed via a subset of electrodes 22 with a pre-recorded biosignal signature, amplitude of frequency band power level threshold or signal template, as described above with respect to FIG. 2, in order to determine whether lead 20 is implanted proximate the target tissue sites. Processor 50 (or a clinician) may use the comparison of a biosignal sensed via a subset of electrodes 22 with the pre-recorded biosignal signature, threshold or template to confirm that a known set of electrodes are positioned proximate to, for example, subthalamic nucleus 90 (e.g., electrodes 22A) and a known set of electrodes are positioned proximate to, for example, substantia nigra 92 (e.g., electrodes 22B). When a characteristic of the biosignal sensed by sensing module 55 (FIG. 2) substantially matches the pre-recorded biosignal signature, threshold or template, the clinician or processor 50 confirms that the electrodes are located near or at subthalamic nucleus 90 and/or substantia nigra 92.

After confirming electrodes 22 are properly positioned within brain 13 to deliver stimulation to the target tissue sites (406), sleep stage detection module 59 may determine a sleep stage (408) and processor 50 can control delivery of electrical stimulation based on the determined sleep stage (410). If the device is not positioned at the target tissue site (406), processor 50 may continue monitoring and analyzing the biosignal until the device is positioned at the target tissue site (402-406).

Figure 10:
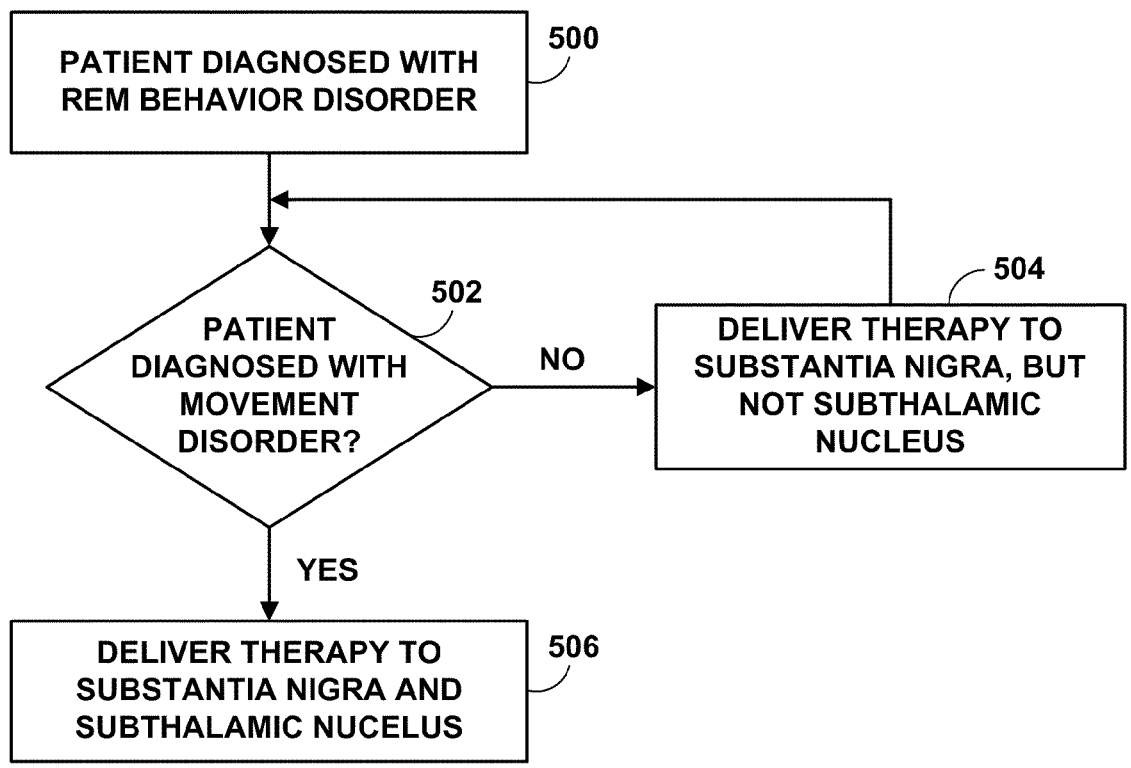
FIG. 10 is a flow diagram illustrating an example technique for independently delivering electrical stimulation to the substantia nigra and the subthalamic nucleus of a patient based on a diagnosis.

FIG. 10 is a flow diagram illustrating an example technique for providing therapy to patient 12 to manage REM behavior disorder. Patients with REM behavior disorder may have trouble initiating sleep or maintaining a particular sleep stage. REM behavior disorder may also, in some cases, act as a precursor to a movement disorder, such as Parkinson's disease.

In some cases, patient 12 may exhibit symptoms associated with REM behavior disorder (RBD), but may not have symptoms associated with Parkinson's disease or another movement disorder. Sometime (e.g., days, weeks, months or even years) after being diagnosed with REM behavior disorder, patient 12 may develop and/or be diagnosed with Parkinson's disease or another movement disorder. There may be a correlation between REM behavior disorder and the onset of a movement disorder (e.g., Parkinson's disease), although the exact correlation is unknown. That is, it is believed that REM behavior disorder may be a precursor to a movement disorder.

Even if patient 12 has not developed or been diagnosed with a movement disorder, it may be desirable to implement DBS system 10 (FIG. 1) to help patient 12 regulate sleep and minimize any disruptions to sleep due to the REM behavior disorder. For example, lead 20 can be implanted to deliver therapy to substantia nigra 92 in order to help patient 12 regulate sleep, e.g., during the REM sleep stage. At a later time, if patient 12 develops a movement disorder and/or is later diagnosed with the movement disorder, therapy delivery to subthalamic nucleus 90 to help manage symptoms of the movement disorder and improve control over motor activity may be implemented.

As shown in FIG. 10, patient 12 may be diagnosed with REM behavior disorder (500). In some cases, a clinician may then determine whether patient 12 also has a movement disorder, such as Parkinson's disease (502). If patient 12 does not have a movement disorder, DBS system 10 may deliver therapy only to substantia nigra 92 in order to treat the REM behavior disorder (504). At that time, patient 12 may not require therapy delivery to subthalamic nucleus 90 because patient 12 has not been diagnosed with a movement disorder. A clinician may continue to monitor patient 12 over the course of days, months, or years in order to determine whether patient 12 has developed a movement disorder (502). If patient 12 develops a movement disorder, such as Parkinson's disease, the clinician may activate delivery of electrical stimulation to subthalamic nucleus 90 in addition to the delivery of stimulation to substantia nigra 92 to treat the movement disorder (506). The techniques described above, e.g., with respect to FIGS. 6-8, can be used to independently control stimulation delivery to subthalamic nucleus 90 and substantia nigra 92.

As discussed previously, therapy system 10 may be configured to independently deliver electrical stimulation to subthalamic nucleus 90 and substantia nigra 92 of patient 12 via, for example, electrodes 22A and 22B (FIGS. 1 and 2). Thus, the configuration of DBS system 10 is conducive to delivery of therapy to treat a REM behavior disorder of patient 12 and, if eventually diagnosed, delivery of therapy to treat a movement disorder of patient 12 without additional implantation of, or, in some cases, without modification to DBS system 10. Additionally or alternatively, activation of therapy to treat the movement disorder may be a subscription feature. For example, a fee or other action or commitment may be required before the subscription to support delivery of electrical stimulation to subthalamic nucleus 90 (i.e., therapy for the movement disorder) is activated.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising, with one or more processors:
   determining a sleep stage of a patient;
   controlling an electrical stimulation device to deliver electrical stimulation to a substantia nigra of a brain of the patient based on the determined sleep stage; and
   controlling the electrical stimulation device to deliver electrical stimulation to a subthalamic nucleus of the brain of the patient based on the determined sleep stage of the patient,
   wherein delivery of electrical stimulation to the substantia nigra and delivery of electrical stimulation to the subthalamic nucleus are independently controlled by the one or more processors.

2. The method of claim 1, wherein determining a sleep stage of a patient comprises receiving a biosignal that is indicative of activity within a brain of the patient and determining the sleep stage based on the biosignal.

3. The method of claim 1, wherein determining a sleep stage of a patient comprises determining whether a patient is in at least one of Stage 1, rapid eye movement, Deep Sleep, or Stage 2 sleep stages.

4. The method of claim 3, wherein controlling the electrical stimulation device to deliver electrical stimulation to the substantia nigra of the patient comprises at least one of activating electrical stimulation, increasing an intensity of electrical stimulation, or decreasing an intensity of electrical stimulation delivered to the substantia nigra if the patient is in at least one of the Stage 1 or rapid eye movement sleep stages, and wherein controlling the electrical stimulation device to deliver electrical stimulation to the subthalamic nucleus of the patient comprises at least one of activating electrical stimulation, increasing an intensity of electrical stimulation, or decreasing an intensity of electrical stimulation delivered to the subthalamic nucleus if the patient is in the at least one of the Stage 1 or rapid eye movement sleep stages.

5. The method of claim 3, wherein controlling the electrical stimulation device to deliver electrical stimulation to the substantia nigra of the patient comprises at least one of activating electrical stimulation, increasing an intensity of electrical stimulation, or decreasing an intensity of electrical stimulation delivered to the substantia nigra if the patient is in the Stage 2 sleep stage, and wherein controlling the electrical stimulation device to deliver electrical stimulation to a subthalamic nucleus of the patient comprises at least one of deactivating electrical stimulation, activating electrical stimulation, increasing an intensity of electrical stimulation, or decreasing an intensity of electrical stimulation delivered to the subthalamic nucleus if the patient is in the Stage 2 sleep stage.

6. The method of claim 3, wherein controlling the electrical stimulation device to deliver electrical stimulation to the substantia nigra of the patient comprises at least one of deactivating electrical stimulation or decreasing the intensity of electrical stimulation delivered to the substantia nigra if the patient is in the Deep Sleep sleep stage, and wherein controlling the electrical stimulation device to deliver electrical stimulation to a subthalamic nucleus of the patient comprises at least one of deactivating electrical stimulation or decreasing the intensity of electrical stimulation delivered to the subthalamic nucleus if the patient is in the Deep Sleep sleep stage.

7. The method of claim 1, further comprising, with the one or more processors:
determining a movement state of the patient; and
controlling the electrical stimulation device to deliver electrical stimulation to the subthalamic nucleus of the patient based on the determined movement state of the patient.

8. The method of claim 1, wherein controlling the electrical stimulation device to deliver electrical stimulation to the substantia nigra comprises controlling the electrical stimulation device to deliver electrical stimulation to the substantia nigra according to a first therapy program and controlling the electrical stimulation device to deliver electrical stimulation to the subthalamic nucleus comprises controlling the electrical stimulation device to deliver electrical stimulation to the subthalamic nucleus according to a second therapy program that is different than the first therapy program.

9. The method of claim 8, wherein controlling the electrical stimulation device to deliver electrical stimulation to the substantia nigra and the subthalamic nucleus comprises controlling the electrical stimulation device to deliver electrical stimulation according to the first and second electrical stimulation therapy programs substantially simultaneously.

10. The method of claim 8, wherein the first and second electrical stimulation therapy programs are delivered alternatively.

11. The method of claim 8, wherein controlling the electrical stimulation device to deliver electrical stimulation according to at least one of the first or second therapy programs comprises modifying at least one therapy parameter value of at least one of the first or second therapy programs based on the determined sleep stage.

12. The method of claim 1, further comprising:
sensing, with a sensing module, a biosignal of the patient via an implanted electrode electrically coupled to the electrical stimulation device; and
determining, with the one or more processors, a location of the implanted electrode within the brain of the patient based on the biosignal.

13. A system comprising:
an electrical stimulation device; and
a processor that determines a sleep stage of a patient, controls the electrical stimulation device to deliver electrical stimulation to a substantia nigra of a brain of the patient based on the determined sleep stage, and controls the electrical stimulation device to deliver electrical stimulation to a subthalamic nucleus of the brain of the patient based on the determined sleep stage of the patient, wherein the processor independently controls the delivery of electrical stimulation to the substantia nigra and the subthalamic nucleus.

14. The system of claim 13, further comprising a sensing module that senses a biosignal that is indicative of activity within the brain of the patient, wherein the processor determines the sleep stage of the patient based on the biosignal.

15. The system of claim 13, wherein the sleep stage comprises at least one of Stage 1, rapid eye movement, Deep Sleep, or Stage 2 sleep stages.

16. The system of claim 15, wherein, if the patient is in at least one of the Stage 1 or rapid eye movement sleep stages, the processor controls the electrical stimulation device to deliver electrical stimulation to the substantia nigra by at least one of activating electrical stimulation, increasing an intensity of electrical stimulation, or decreasing an intensity of electrical stimulation delivered to the substantia nigra, and wherein the processor controls the electrical stimulation device to deliver electrical stimulation to the subthalamic nucleus by at least one of activating electrical stimulation, increasing an intensity of electrical stimulation, or decreasing an intensity of electrical stimulation delivered to the subthalamic nucleus.

17. The system of claim 15, wherein, if the patient is in the Stage 2 sleep stage, the processor controls the electrical stimulation device to deliver electrical stimulation to the substantia nigra by at least one of activating electrical stimulation, increasing an intensity of electrical stimulation, or decreasing an intensity of electrical stimulation delivered to the substantia nigra, and wherein the processor controls the electrical stimulation device to deliver electrical stimulation to the subthalamic nucleus by at least one of deactivating electrical stimulation, activating electrical stimulation, increasing an intensity of electrical stimulation, or decreasing an intensity of electrical stimulation delivered to the subthalamic nucleus.

18. The system of claim 15, wherein, if the patient is in the Deep Sleep sleep stage, the processor controls the electrical stimulation device to deliver electrical stimulation to the substantia nigra by at least one of deactivating electrical stimulation or decreasing the intensity of electrical stimulation delivered to the substantia nigra, and wherein the processor controls the electrical stimulation device to deliver electrical stimulation to the subthalamic nucleus of the patient by at least one of deactivating electrical stimulation or decreasing the intensity of electrical stimulation delivered to the subthalamic nucleus.

19. The system of claim 13, wherein the processor determines a movement state of the patient and controls the electrical stimulation device to deliver electrical stimulation to the subthalamic nucleus of the patient based on the determined movement state of the patient.

20. The system of claim 13, wherein the processor controls the electrical stimulation device to deliver electrical stimulation to the substantia nigra according to a first therapy program and controls the electrical stimulation device to deliver electrical stimulation to the subthalamic nucleus according to a second therapy program that is different than the first therapy program.

21. The system of claim 20, wherein the processor controls the electrical stimulation device to substantially simultaneously deliver electrical stimulation to the substantia nigra and the subthalamic nucleus according to the first and second therapy programs, respectively.

22. The system of claim 20, wherein the processor controls the electrical stimulation device to alternatively deliver electrical stimulation to the substantia nigra and the subthalamic nucleus according to the first and second therapy programs, respectively.

23. The system of claim 13, further comprising a sensing module that senses a biosignal that is indicative of activity within a brain of the patient via an electrode electrically coupled to the electrical stimulation device, wherein the processor determines a location of the electrode within the brain of the patient based on the biosignal.

24. A non-transitory computer-readable medium comprising instructions that cause a programmable processor to:
determine a sleep stage of a patient based on a brain signal sensed within a brain of the patient;

control an electrical stimulation device to deliver electrical stimulation to a substantia nigra of the brain of the patient based on the determined sleep stage; and control the electrical stimulation device to deliver electrical stimulation to a subthalamic nucleus of the brain of the patient based on the determined sleep stage of the patient, wherein the instructions cause the programmable processor to independently control the electrical stimulation to deliver stimulation to the substantia nigra and the subthalamic nucleus.

25. The non-transitory computer-readable medium of claim 24, further comprising instructions that cause the programmable processor to determine a location of an implanted electrode within the brain of the patient based on a biosignal sensed by a sensing module via the implanted electrode.

26. A system comprising:
means for generating and delivering electrical stimulation to a brain of a patient;
means for determining a sleep stage of a patient;
means for controlling the means for generating and delivering electrical stimulation to deliver electrical stimulation to a substantia nigra of the brain of the patient based on the determined sleep stage; and
means for controlling the means for generating and delivering electrical stimulation to deliver electrical stimulation to a subthalamic nucleus of the brain of the patient based on the determined sleep stage of the patient, wherein the means for controlling the means for generating and delivering electrical stimulation to deliver electrical stimulation to the subthalamic nucleus controls the delivery of electrical stimulation to the subthalamic nucleus independently of the delivery of electrical stimulation to the substantia nigra.

27. The system of claim 26, further comprising means for sensing a biosignal that is indicative of activity within a brain of the patient, wherein the means for determining the sleep stage of the patient determines the sleep stage based on the biosignal.

28. The system of claim 26, further comprising:
means for sensing a biosignal of the patient via an implanted electrode electrically coupled to the means for generating and delivering electrical stimulation to the brain of the patient; and
means for determining a location of the implanted electrode within the brain of the patient based on the biosignal.

* * * * *